(12) United States Patent
Yeh et al.

(10) Patent No.: US 6,238,866 B1
(45) Date of Patent: May 29, 2001

(54) DETECTOR FOR NUCLEIC ACID TYPING AND METHODS OF USING THE SAME

(75) Inventors: Homer R. Yeh, Baltimore; Charles H. Wick, Darlington, both of MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/246,277

(22) Filed: Feb. 8, 1999

Related U.S. Application Data

(63) Continuation of application No. 08/838,157, filed on Apr. 16, 1997, now abandoned, which is a continuation of application No. 06/015,965, filed on Apr. 16, 1996.

(51) Int. Cl.[7] .................................................. C12Q 1/68
(52) U.S. Cl. .............................. 435/6; 536/23.1; 422/68.1
(58) Field of Search ............................. 435/6, 91.1, 91.2; 536/23.1

(56) References Cited

U.S. PATENT DOCUMENTS 5,427,932 * 6/1995 Weier et al. .................... 435/91.2

* cited by examiner

Primary Examiner—Ardin H. Marschel
(74) Attorney, Agent, or Firm—Ulysses John Biffoni; Vincent J. Ranucci

(57) ABSTRACT

The present invention provides devices and methods for detecting or characterizing a nucleic acid analyte without requiring electrophoresis or the direct sequencing of analyte samples or analyte fragments. The device includes a panel or array of double stranded oligonucleotide probes immobilized on a solid support. each probe comprising a nucleotide sequence having a hypervariable number of tandem repeat sequences. Desirably, the specificity of the probes is varied with the location on the panel or array. One strand of each probe is preferably anchored at one terminus to a solid support and the opposite terminus of a second strand is not so anchored. The probes and/or the analyte are labeled by one or more reporter moieties, designed, for example, to allow for visual or instrument based detection of hybridization events.

1 Claim, 4 Drawing Sheets

SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:

```
        (A) LENGTH: 29 base pairs
        (B) TYPE: nucleic acid
        (C) STRANDEDNESS: not relevant
        (D) TOPOLOGY: not relevant (ii) MOLECULE TYPE: DNA (genomic)

(iii) HYPOTHETICAL: NO (iv) ANTI-SENSE: NO (vi) ORIGINAL SOURCE:
        (A) ORGANISM: Epstein-Barr virus (viii) POSITION IN GENOME:
        (B) MAP POSITION: 102581 to 102652
        (C) UNITS: bp (xi) SEQUENCE DESCRIPTION: SEQ ID NO: 1:

AAGCCCCACC ATCCGCTGCC GCCCTCCAT                                            29

(2) INFORMATION FOR SEQ ID NO: 2:

(i) SEQUENCE CHARACTERISTICS:
        (A) LENGTH: 31 base pairs
        (B) TYPE: nucleic acid
        (C) STRANDEDNESS: not relevant
        (D) TOPOLOGY: not relevant (ii) MOLECULE TYPE: DNA (genomic)

(iii) HYPOTHETICAL: NO (iv) ANTI-SENSE: NO (vi) ORIGINAL SOURCE:
        (A) ORGANISM: Epstein-Barr virus (viii) POSITION IN GENOME:
        (B) MAP POSITION: 102581 to 102652
        (C) UNITS: bp (xi) SEQUENCE DESCRIPTION: SEQ ID NO: 2:

GAGGCCCCAC CGTCCGCTGC CGCCCCTCCT T                                         31

(2) INFORMATION FOR SEQ ID NO: 3:

(i) SEQUENCE CHARACTERISTICS:
        (A) LENGTH: 32 base pairs
        (B) TYPE: nucleic acid
        (C) STRANDEDNESS: not relevant
        (D) TOPOLOGY: not relevant (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (viii) POSITION IN GENOME:
        (A) CHROMOSOME/SEGMENT: 33.15 minisatellite (xi) SEQUENCE DESCRIPTION: SEQ ID NO: 3:

AGAGGTGGGC AGGTGGAGAG GTGGGCAGGT GG                                        32

(2) INFORMATION FOR SEQ ID NO: 4:

(i) SEQUENCE CHARACTERISTICS:
        (A) LENGTH: 22 base pairs
        (B) TYPE: nucleic acid
```

```
        (C) STRANDEDNESS: not relevant
        (D) TOPOLOGY: not relevant (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (viii) POSITION IN GENOME:
        (A) CHROMOSOME/SEGMENT: 33.6 minisatellite (xi) SEQUENCE DESCRIPTION: SEQ ID NO: 4:

TGGAGGAGGG CTGGAGGAGG GC                                               22

(2) INFORMATION FOR SEQ ID NO: 5:

(i) SEQUENCE CHARACTERISTICS:
        (A) LENGTH: 26 base pairs
        (B) TYPE: nucleic acid
        (C) STRANDEDNESS: not relevant
        (D) TOPOLOGY: not relevant (ii) MOLECULE TYPE: DNA (genomic)

(iii) HYPOTHETICAL: NO (vi) ORIGINAL SOURCE:
        (A) ORGANISM: Homo sapiens (viii) POSITION IN GENOME:
        (B) MAP POSITION: MS1 minisatellite (xi) SEQUENCE DESCRIPTION: SEQ ID NO: 5:

AGGGTGGAYA GGGTGGAYAG GGTGGA                                           26

(2) INFORMATION FOR SEQ ID NO: 6:

(i) SEQUENCE CHARACTERISTICS:
        (A) LENGTH: 30 base pairs
        (B) TYPE: nucleic acid
        (C) STRANDEDNESS: not relevant
        (D) TOPOLOGY: not relevant (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (viii) POSITION IN GENOME:
        (A) CHROMOSOME/SEGMENT: CMM101 minisatellite (xi) SEQUENCE DESCRIPTION: SEQ ID NO: 6:

TCCACCTCAG CCCCCTCCAC CTCAGCCCCC                                       30

(2) INFORMATION FOR SEQ ID NO: 7:

(i) SEQUENCE CHARACTERISTICS:
        (A) LENGTH: 31 base pairs
        (B) TYPE: nucleic acid
        (C) STRANDEDNESS: not relevant
        (D) TOPOLOGY: not relevant (ii) MOLECULE TYPE: DNA (genomic)

(iii) HYPOTHETICAL: NO
```

(iv) ANTI-SENSE: NO (vi) ORIGINAL SOURCE:
            (A) ORGANISM: Homo sapiens (viii) POSITION IN GENOME:
            (A) CHROMOSOME/SEGMENT: YNH24 Minisatellite (xi) SEQUENCE DESCRIPTION: SEQ ID NO: 7:

AACAACCCCA CTGTACTTCC CACTGCTCCT G                                          31

(2) INFORMATION FOR SEQ ID NO: 8:

(i) SEQUENCE CHARACTERISTICS:
            (A) LENGTH: 27 base pairs
            (B) TYPE: nucleic acid
            (C) STRANDEDNESS: not relevant
            (D) TOPOLOGY: not relevant (ii) MOLECULE TYPE: DNA (genomic)

(iii) HYPOTHETICAL: NO (iv) ANTI-SENSE: NO (vi) ORIGINAL SOURCE:
            (A) ORGANISM: Homo sapiens (viii) POSITION IN GENOME:
            (A) CHROMOSOME/SEGMENT: EFD52 Minisatellite (xi) SEQUENCE DESCRIPTION: SEQ ID NO: 8:

TACTAGCACW SYCCTGGYTA CTAGCAC                                               27

(2) INFORMATION FOR SEQ ID NO: 9:

(i) SEQUENCE CHARACTERISTICS:
            (A) LENGTH: 31 base pairs
            (B) TYPE: nucleic acid
            (C) STRANDEDNESS: not relevant
            (D) TOPOLOGY: not relevant (ii) MOLECULE TYPE: DNA (genomic)

(iii) HYPOTHETICAL: NO (iv) ANTI-SENSE: NO (vi) ORIGINAL SOURCE:
            (A) ORGANISM: Homo sapiens (viii) POSITION IN GENOME:
            (A) CHROMOSOME/SEGMENT: TBQ7 minisatellite (xi) SEQUENCE DESCRIPTION: SEQ ID NO: 9:

TGCCTGAGCC TTCTCACAGT CTCACCTGAT C                                          31

(2) INFORMATION FOR SEQ ID NO: 10:

(i) SEQUENCE CHARACTERISTICS:
            (A) LENGTH: 25 base pairs
            (B) TYPE: nucleic acid
            (C) STRANDEDNESS: not relevant
            (D) TOPOLOGY: not relevant (ii) MOLECULE TYPE: DNA (genomic)

(iii) HYPOTHETICAL: NO (iv) ANTI-SENSE: NO (vi) ORIGINAL SOURCE:

(A) ORGANISM: Homo sapiens (viii) POSITION IN GENOME:
          (A) CHROMOSOME/SEGMENT: MS43 minisatellite (xi) SEQUENCE DESCRIPTION: SEQ ID NO: 10:

CCTTCCCGGG GCCCTCCCTA TACCC                                              25

(2) INFORMATION FOR SEQ ID NO: 11:

(i) SEQUENCE CHARACTERISTICS:
          (A) LENGTH: 17 base pairs
          (B) TYPE: nucleic acid
          (C) STRANDEDNESS: not relevant
          (D) TOPOLOGY: not relevant (ii) MOLECULE TYPE: DNA (genomic)

(iii) HYPOTHETICAL: NO (iv) ANTI-SENSE: NO (vi) ORIGINAL SOURCE:
          (A) ORGANISM: Homo sapiens (viii) POSITION IN GENOME:
          (A) CHROMOSOME/SEGMENT: JE46 minisatellite (xi) SEQUENCE DESCRIPTION: SEQ ID NO: 11:

CCCCCCGTGT CGCTGTT                                                       17

(2) INFORMATION FOR SEQ ID NO: 12:

(i) SEQUENCE CHARACTERISTICS:
          (A) LENGTH: 630 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (A) ORGANISM: Epstein-Barr virus (viii) POSITION IN GENOME:
          (B) MAP POSITION: 7421 to 8042
          (C) UNITS: bp (xi) SEQUENCE DESCRIPTION: SEQ ID NO: 12:

ATATRVATKG GGATAGCATA TVCTACCCRG ATATRVATKG GGATAGCATA TVCTACCCRG         60

ATATRVATKG GGATAGCATA TVCTACCCRG ATATRVATKG GGATAGCATA TVCTACCCRG        120

ATATRVATKG GGATAGCATA TVCTACCCRG ATATRVATKG GGATAGCATA TVCTACCCRG        180

ATATRVATKG GGATAGCATA TVCTACCCRG ATATRVATKG GGATAGCATA TVCTACCCRG        240

ATATRVATKG GGATAGCATA TVCTACCCRG ATATRVATKG GGATAGCATA TVCTACCCRG        300

ATATRVATKG GGATAGCATA TVCTACCCRG ATATRVATKG GGATAGCATA TVCTACCCRG        360

ATATRVATKG GGATAGCATA TVCTACCCRG ATATRVATKG GGATAGCATA TVCTACCCRG        420

ATATRVATKG GGATAGCATA TVCTACCCRG ATATRVATKG GGATAGCATA TVCTACCCRG        480

ATATRVATKG GGATAGCATA TVCTACCCRG ATATRVATKG GGATAGCATA TVCTACCCRG        540

ATATRVATKG GGATAGCATA TVCTACCCRG ATATRVATKG GGATAGCATA TVCTACCCRG        600

ATATRVATKG GGATAGCATA TVCTACCCRG                                         630

```
(2) INFORMATION FOR SEQ ID NO: 13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Epstein-Barr virus (viii) POSITION IN GENOME:
        (B) MAP POSITION: 7421 to 8042
        (C) UNITS: bp (xi) SEQUENCE DESCRIPTION: SEQ ID NO: 13:

GCGCRDGCMA AAGCGATGCG CDTCGTTTRA                                      30
```

DETECTOR FOR NUCLEIC ACID TYPING AND METHODS OF USING THE SAME

This application is a continuation of application Ser. No. 08/838,157, filed on Apr. 16, 1997, now abandoned which in turn is a nonprovisional continuation of provisional application Serial No. 06/015,965, filed on Apr. 16, 1996

GOVERNMENT INTEREST

The invention described herein may be manufactured, licensed, and used by or for the U.S. Government.

BACKGROUND OF THE INVENTION

1. Field of the Invention

The invention is generally related to the field of detecting and identifying genetic materials. such as nucleic acid molecules of interest, using a nucleic acid detector. The nucleic acid detector according to the invention is constructed from double stranded hybridization probes that are immobilized on a support, to form a DNA detector. The DNA detector is formed into an array of varied binding specificities that is capable of detecting multiple genetic loci. The probes are oligonucleotides each comprising a hypervariable number of tandem repeats ("VNTR") that are anchored at one terminus to a support and at the other terminus to a reporter moiety.

2. Description of the Related Art

Previously, the best method known for detecting and identifying a nucleic acid analyte (e.g., an unknown sample) has been so-called DNA fingerprinting, which relies on a comparison of the electrophoretic migration of restriction fragments of an unknown nucleic acid analyte to the electrophoretic migration pattern of a known genomic sample subjected to identical restriction treatment. This process is typically, but not exclusively, employed to identify or detect deoxyribonucleic acid ("DNA"). Variations on this process are known, including the use of specific hybridization probes to enhance accuracy by confirming that migration bands are homologous to specific nucleic acid sequences of interest. This is possible because restriction enzymes cleave DNA at specific loci, which will vary (i.e., exhibit polymorphism) with each genome. Thus, when DNA gel banding techniques where developed, it seemed possible that the technique would provide unique and unequivocal comparisons and identification between genomic samples.

DNA fingerprinting has been relied upon to analyze forensic evidence, for example, to obtain evidence of the identity of genetic material for criminal or paternity proceedings. The technique is also used to identify human remains or to determine species relatedness. DNA fingerprinting using VNTR loci complementary probes is useful not only in a forensic laboratory setting to provide individual identification and paternity testing, but also has been extensively used for the investigation of taxonomic relationship among fish, birds, plants, wild and domestic animals. In addition, it has also been used for clarifying genetic relationship among related species, for discriminating pathogens from non-pathogens, and for determining the effect of environmental factors on evolutionary dynamics and speciation of microorganisms.

Of course, as the artisan will appreciate, the accuracy of the DNA fragment size-sharing principle has been the subject of criticism e.g., in numerous legal cases, because similarities in the electrophoretic mobility, e.g., size, of restriction fragments on DNA electrophoretic profiles does not unequivocally establish the full characteristics of the alleles.

Therefore, greater accuracy was required before DNA gel banding techniques would be accepted as an accurate means of genetic profiling. While the classical genetic markers. such as the single-locus probe (SLP), have been employed in an attempt to provide improved identification. these usually give little information about the individualization of species due to the very large number of SLP's necessary to determine the exact relationship between species. The use of multiple SLPs for identification purposes has been known as "multiplexing."[15]

In 1985, geneticist Alec Jeffreys (Jeffreys, et al., 1985, Nature 314:67–73) partially solved the accuracy problem by applying certain specific hybridization probes to electrophoresis patterns produced by DNA restriction fragments. Since then. while DNA profiling has become an accepted scientific and forensic tool, a great deal of public controversy has continued to be generated by these methods, particularly when used for forensic identifications.

The method described by Jeffreys et al., supra, was based on DNA gel banding techniques with the added feature of detecting polymorphisms in minisatellite DNA. The term "satellite" was originally derived from the observation that DNA isolated from eukaryotes under buoyant density gradient ultracentrifugation, shows extra peaks beside the major DNA bands (Bretton. R J et al., 1968. Science 161: 529–540). Satellites are relatively large chromosomal structures which contain millions of repetitive sequences. Similar repetitive sequences were later found to be almost universally present in the genomic structures of most eukaryotes, as well as in genome viruses. These sequences were called "minisatellites", "midisatellites", and "microsatellites" because of their limited degrees of repetition, i.e., small size (Jeffreys et al., 1985, supra) relative to "satellites", which contain millions of repetitive sequences.

For example, the term, "minisatellite" is applied to any of a class of dispersed arrays of short (e.g., 10–50 bp) tandem direct repeat motifs that contain variants of a common core sequence (e.g., 10–15 bp). The majority of minisatellites are distributed at the terminal ends of genomes. Although their exact functions are not clearly known these terminal repeats may play a significant role in replication control of genes. The major difference of TR's from classical genetic markers is in the hypervariable number of the tandem repeats (VNTR). The VNTR therefore provides extremely useful information about relatedness and individualization of species and other types of nucleic acid analytes.

The human-derived minisatellites such as 33.6,33.15, MS1, CMM1O 1YNH24, EFDS2, TBQ7, MS43 and JE46 are commonly used to prepare hybridization probes for forensic testing, for example, to provide individual identification and paternity testing. These minisatellites can also hybridize to DNA isolated from avians, plants, fish, and other mammals[3-6], thus indicating the presence of common genetic structures in these living organisms.

The multiloci human probes 33.6, 33.15, and MS1 have been used for fingerprinting of DNA isolated from pigs, mice, and common marmosets,[3] for characterization of genetic relationship between breedings of poultry, and for studying a population of foxes in the California Channel Islands.[8] Application of the multilocus fingerprinting probe (MLP) 33.15 also revealed genetic profiles in species and strains of Leishmania and *Trypanosoma cruzi*.[9] Fingerprinting data can permit the construction of pedigrees that reflect the population history and the geographical distance of different species and strains of the parasites.

Another type of abundantly distributed repetitive sequences are the microsatellites, which have an even smaller degree of repetition than that of the minisatellites. They are distinguishable from minisatellites by having repetition within the repetitive units. The majority of minisatellites are usually distributed at the terminal ends of genes, while microsatellites are widespread along the chromosomes. Microsatellites used extensively for DNA-fingerprinting have the general structural characteristics of (CA)8, (CT)8, (CAC)5, (GAC)5, (GACA)4, (GATA)4, and the like. They are abundantly distributed in genomic structures of living organisms. Dinucleotide repeats, particularly CA/GT repeats, are very abundant and polymorphic. In other words, they are extremely variable in number of the repeat units. [13] Using (GTG), (GACA) or phage M13 core sequence as either hybridization probes or primers in combination with restriction enzymes with a recognition site of 6 base pairs (bp), over 70 species representing 18 genera filamentous fungi and 5 genera of yeasts were fingerprinted, and their DNA banding patterns and taxonomic relationship were clearly identified. [14] These ubiquitously interspersed, tandemly repetitive sequences with a total number of bases ranging from 2 to 6 are highly polymorphic, rendering these simple short tandemly repeated sequences superior to other polymorphic sequences for individual and species identification purposes. Results obtained from DNA-fingerprinting using either minisatellites or microsatellites agree well with traditional taxonomic classification based on morphological characteristics.

Minisatellite and microsatellite DNA probing of DNA fragments has advantages over conventional restriction fragment length DNA-polymorphism. It is relatively rapid, simple, and reliable, as well as more easily applicable to large scale experiments. Application of VNTR sequences as complementary probes for DNA gel banding techniques yields electrophoretic patterns substantially unique to each individual and species or strain. As for the processes conducted with conventional probes, these assays are also commonly referred to "DNA fingerprinting."

Essentially, genomic material or forensic material believed to contain genomic material is subjected to cleavage by one or more restriction enzymes as discussed above. Electrophoretic separation of the restriction fragments followed by contact with labeled VNTR probes specifically complementary to specific regions of the cleaved genomic DNA produces the DNA profile or fingerprint.

If, for example, two samples of genetic material produce sufficiently matching DNA gel banding and VNTR labeling patterns (i.e., the two samples cleave into fragments of the same size, migrating the same distance on the gel, and have homologous regions complementary to the same VNTR loci), the conclusion is that the samples are from the same source, to a high degree of probability.

According to Chakrabarty and Jin,[19] more than 50 SLP's may be needed for positive identification of an individual or species. A single SLP could only detect a piece of DNA sequence among huge genomes of living cells, yielding little information as to what has been detected. In comparison, when multi-locus probes ("MLP") such as minisatellites or microsatellites are used, it is estimated that only about 7 minisatellites and 15 microsatellites may be required for positive individual or species identification. For simultaneous typing with MLP, a panel of nucleic acid detector molecules are constructed (exemplified by Table 1, presented hereinbelow) according to the known information of VNTR's of the particular species to be studied. Binding patterns as well as the binding characteristics of each member of the panel can be monitored simultaneously. When nucleic acid found in an analyte specimen is considered to be identical to that obtained from an individual, all patterns and characteristics of bindings must match each other well for positive identification. Relatedness among individuals and species can be also calculated from the similarity index(x) or "alleles sharing coefficient" (D) according to the total number of the shared alleles and total number of alleles present from data obtained from a panel of binding assays.

Statistical Considerations Of Relatedness Among Individuals And Species

The basic principle for application of allele sharing for individual/species and relatedness determination is based on the number of loci and the number of shared alleles of genotypes of individual entities. For quantifying the differences between two DNA fingerprinting profiles, "band-sharing coefficients" (D) or similarity indices (x) have been used, and the relationship between the two individuals can be estimated according to the following equations (according to references 1, 16, 17, 18 and 19, provided hereinbelow).

$$D = 2Nab/(Na+Nb) \quad (1)$$

$$x = ((Nab/Na)+(Nab/Nb))/2 \quad (2).$$

Nab is the number of scorable bands to two DNA profiles A and B. Na is the number of scorable bands in A. Nb is the number of scorable bands in B. The band-sharing values obtained from the above equations yield similar results. In humans, band-sharing coefficient, D or similarity index x is about 0.2 for a pair of unrelated individuals.[16] The average values could reach 0.8 between siblings and between parents and offspring.[17-18] In plants, the average band-sharing coefficient can reach 0.5 due to vegetative method of propagation. When in-breeding rate is high among those populations, D or x values are also high. For DNA fingerprints derived from the same individual, as in the cases of forensic specimen analysis, Nab=Nb=Na, and the D or x value is equal to one.

Thus, from a statistical point of view, the application of the VNTR loci to conventional DNA fingerprinting methods, by providing a multiplicity of loci for comparison. has improved the accuracy and reliability of DNA profiling by enhancing confidence in the significance of bands of the same size in two samples under comparison.

However, problems remain. It has been argued in numerous forensic legal proceedings that DNA fragments that have same sizes, although they migrate to the same positions in agarose gel, are not necessarily identical in their actual sequences unless all fragments of the electrophoresis profiles are measured. Heretofore, sequence analysis of multiple DNA fingerprint bands to produce unequivocal identification data has been deemed impractical because of the tedious, time-consuming, and costly procedures involved in such DNA sequencing.

Although MLP's reduce the total number of probes required for reliable identification, there remains the requirement for electrophoretic separation of genomic fragments before such MLP probes can be applied to DNA fingerprinting methods. In addition, the previously employed DNA fingerprinting technique described above, even when conducted using VNTR probes, remains a tedious and time consuming process requiring sophisticated laboratory facilities. Further. the technique must be performed by an individual with extensive training in molecular biology and chemistry and certainly cannot readily be practiced under field conditions, e.g., outside of a laboratory.

Therefore, it is clear that alternative methods for rapid, accurate and simple methods for biological detection or identification of nucleic acid analytes are required. The art has attempted to provide alternative techniques. For example, one art-known alternative to gel banding techniques is the use of non-gel capillary electrophoresis and the nuclei condensation electrospray to provide size separation and fractionation of macromolecules.[20] However, this technique can only provide information about the size of each DNA fragment obtained from restriction digest. Since no detailed sequence information can be derived from this procedure. the problem of distinguishing differing genomic fragments, which nevertheless have the same measured molecular weight, remains unresolved. Moreover. as for the agarose gel electrophoresis previously described, application of sample to the non-gel capillary is also challenging and requires highly skilled practitioners.

It is therefore clear that. despite the foregoing efforts, there remains a need in the art for new approaches to nucleic acid profiling that are applicable for initial screening purposes for large numbers of samples (e.g., species and individuals), able to be conducted without sophisticated instrumentation. For example, there is a need for nucleic acid profiling methods that avoid the use of electrophoresis and can be conducted, for example, under field, or even battlefield, conditions, in order to obtain reliable identification or characterization of genomic material (e.g., identification of pathogen. animal and/or human tissue samples). In particular, it would be desirable to have available a DNA/RNA detection method that does not require elaborate and complex processes to conduct prehybridization. hybridization. linkage, blottings (Southern or Northern), electrophoresis and other manipulation steps.

OBJECTS OF THE INVENTION

It is therefore an object of the invention to provide new devices and methods for genetic analysis for individual and species identification that are both simple and reliable, compared to previously available methods, and readily applied outside of a laboratory environment.

It is a further object of the present invention to provide methods for detecting or characterizing a nucleic add analyte without the application of gel electrophoresis and other tedious and time-consuming DNA/RNA analytical procedures such as prehybridization, hybridization, blottings (Southern and Northern), linkage and other complex other laboratory processes.

It is a further object of the present invention to provide new devices and methods for profiling genomic material, such as nucleic acids, the devices and methods being based on hybridization activity of one or more analytes by multiple VNTR hybridization probes.

It is a yet further object of the present invention to provide new devices and methods for hybridization-based genotyping that are based on the VNTR polymorphism of the tested genome to provide high specificity and accuracy without the necessity for electrophoresis of genomic fragments and/or sequencing of genomic fragments and/or without the necessity for an impractically large number of conventional probes of single allelic specificity.

It is a yet further object of the present invention to provide devices and methods for hybridization-based genotyping that utilize multiple copies VNTR probes that are based on micro and minisatellite DNA. in order to enhance the accuracy of the genotyping results while minimizing the number of probes required.

SUMMARY OF THE INVENTION

In accordance with the above objects and others which will be apparent from the further reading of the specification and of the appended claims. the present invention is related to the surprising discovery that immobilized panels and/or arrays of nucleic acid probe molecules, that are polymorphic for VNTR regions of minisatellites, midisatellites, and microsatellites, serve as very specific hybridizable detectors of particular nucleic acid analytes of interest.

Accordingly, the invention provides for a device and methods for detecting or characterizing a nucleic acid analyte. The device preferably includes a panel or array of double stranded oligonucleotide probes immobilized on a solid support, each probe comprising a first nucleic acid strand having a hypervariable number of tandem repeat sequences and a second strand that complements the first strand. The artisan will appreciate that the complementation between the first and second strands need not represent perfect homology, but should be sufficient to permit hybridization and annealing under stringent conditions.

Desirably, the specificity of the probes is varied with the location on the panel or array so that the degree of homology of the analyte is determined for each of the VNTR loci of interest, each represented by a specific location on the panel, permitting ready comparison of different analytes, e.g., a known virus and a collected sample or a known forensic sample and a forensic sample found at a crime scene.

One strand of each probe is preferably anchored at one terminus to a solid support and the opposite terminus of a second strand is not so anchored. The probes and/or the analyte are labeled by one or more reporter moieties, designed, for example, to allow for visual or instrument-based detection of hybridization events by a characteristic pattern of successful binding events.

In addition, the probes are selected to be hybridizable to a plurality of nucleic acid sequences or genetic loci of selected analyte or analytes, preferably based on VNTR loci. Upon denaturation and renaturation of the probe in the presence of a detectable analyte, the analyte hybridizes to a strand of the probe, thereby causing a reporter moiety to be detected, in proportion to the amount of said analyte present. Either the probe or the analyte can be labeled with a detectable reporter moiety.

Thus, in one aspect of the invention, a strand of the probe is labeled with a reporter moiety. In addition, each hybridizable location on the panel can be labeled with a distinctive reporter moiety, e.g., distinguished by color, fluorescence, enzyme activity and the like, so that the binding properties of the analyte may be characterized (visually or by electronic sensors) by the resulting pattern of successful hybridization.

In another aspect of the invention, the analyte is subjected to a labeling process before application of the analyte to the device, so that the analyte is labeled with a suitable reporter moiety. Optionally, both the analyte and the probe are labeled with suitable distinguishable reporter moieties, so that both may be monitored.

Thus, the process of the invention provides for detection of specific nucleic acid sequences or genetic loci by hybridization, preferably under stringent conditions, after, for example, thermal cycling, to complementary immobilized oligonucleotide probes. If the second (non-immobilized) strand of the double stranded probe is labeled with a reporter moiety, successful hybridization by the immobilized strand displaces the second strand into the assay medium where a rise in the level of the reporter moiety is detected. If the analyte is labeled. hybridization to oligonucleotide probes on the panel results in a decrease in reporter moiety in the assay solution and an increase in reporter moiety on the panel surface.

The reporter moiety can be measured, for example, by means of a visually detectable "signal," or "reporter signal," e.g., a color signal, a luminescent signal, a fluorescent signal, generation of an enzyme reaction product from the reaction of a suitable substrate by an enzyme able to provide a signal in the presence of a suitable substrate. and/or a radioisotope reporter and combinations thereof.

The device can be opaque, transparent or translucent, but it is preferred that at least a part of the device is transparent or translucent when the reporter moiety is to be visually detected, e.g., by visual or instrumented detection of color or emitted light.

The device may include a solid surface and/or chamber and/or array of chambers or test wells. in any suitable shape for conducting the assay according to the invention. In another aspect, the device may include a plurality of particles, microspheres, beads or spheroids as a solid support system for probe, analyte and/or mixtures thereof.

The invention contemplates applying any of the numerous art-known devices that have been used for immobilization of proteins, enzymes, and nucleic acids on different solid supports such as microspheres, filter papers (containing —COOH, —NH2, —OH, —SH, and any other suitable art-known functional chemical groups), nylon and other synthetic fibers, microscope slides, pore glass beads, magnetic microspheres, silica gel, absorbants, and many others, as described, simply by way of example, in the appropriate sections of the multivolume reference series, *Methods of Enzymology*, (New York. Academic Press) the disclosures of which are incorporated herein by reference in their entireties.

The artisan will appreciate that the oligonucleotide DNA detector molecules or probes according to the invention can readily be prepared from any satellite and/or minisatellite genomic sequences or fragments known to the art, or yet to be discovered, and/or nucleic acid sequences of microorganisms of interest. Simply by way of example, and without limitation. the invention contemplates the use of VNTR sequences or fragments, such as. for example, human-derived minisatellites such as 33.6, 33.15, MS1, CMM1O1, YNH24, EFDS2, TBQ7, MS43 and JE46. Nucleic acid sequences of any art known microorganisms of interest may be employed, including, for example, a fragment of an Epstein-Barr virus genome spanning from about nucleotide 7421 to about nucleotide 8042.

The device and reagents and assay control samples according to the invention are desirably prepared in the form of a kit for detecting or characterizing a nucleic acid analyte in packaged combination with known quantities of one or several control analytes for normalizing the detection process and optionally a calibrated color chart for aiding visual determinations of successful detection.

DETAILED DESCRIPTION OF THE PREFERRED EMBODIMENT

Figure 1:
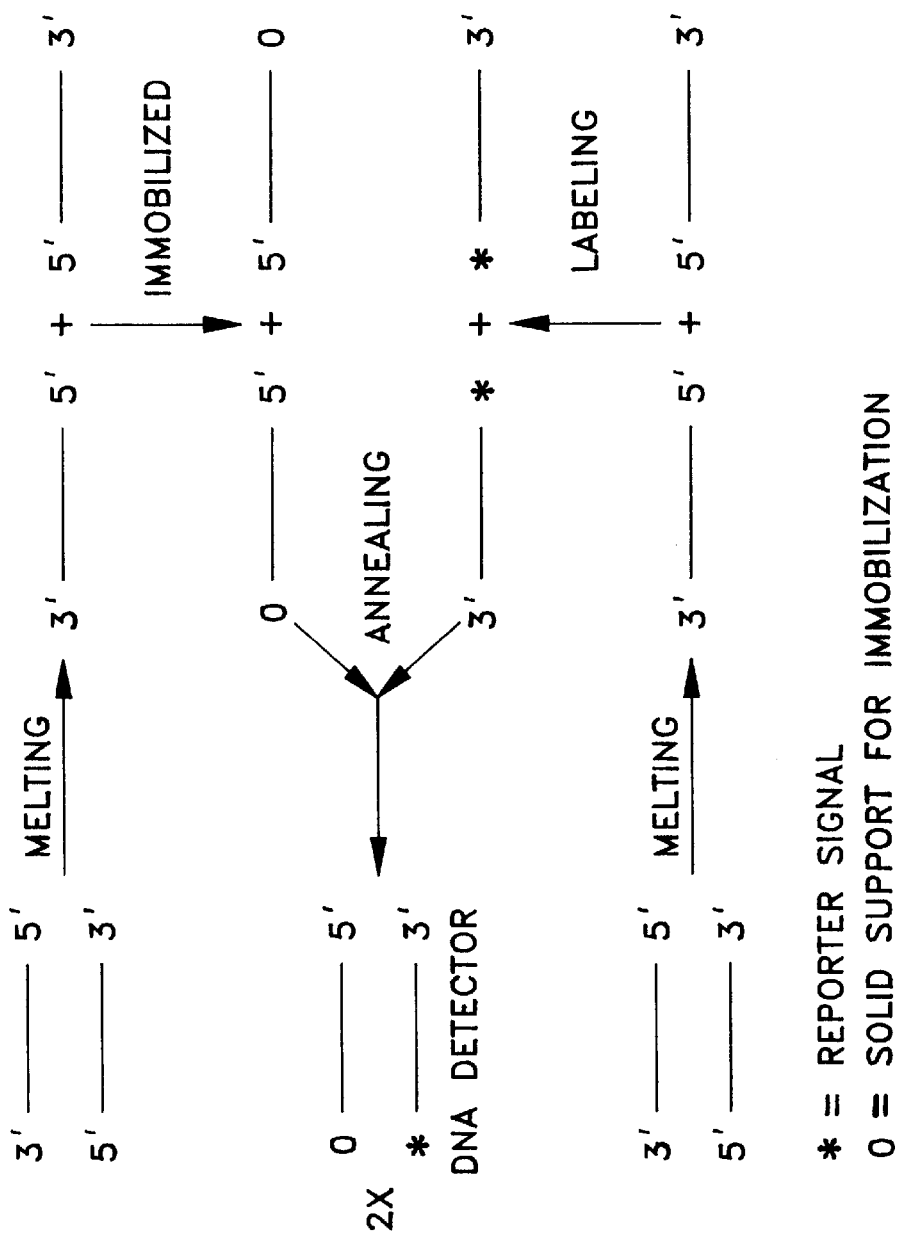
FIG. 1 depicts the method used for construction of nucleic acid detector molecules used for genotyping of individuals and species.

Accordingly, the present invention provides methods and devices for genotyping a sample by hybridization of an analyte to an array of VNTR-based hybridization probes under stringent conditions.

As used herein, the term "analyte," unless otherwise indicated, includes plural analytes, i.e., a substance or substances, either alone or in admixtures, whose presence is to be detected and, if desired, quantitated. The analyte may be a polynucleotide, including an DNA or RNA molecule of small or high molecular weight, including a genomic fragment, a molecular complex including those molecules, or a biological system containing nucleic acids, such as a virus, a cell, or group of cells. Among the common analytes are nucleic acids (DNA and RNA) or segments thereof, oligonucleotides, either single- or double-stranded, and samples of biological material containing such nucleic acids such as. for example. viruses, bacteria. cells in culture. tissue specimens. blood, hair. nails and the like. Thus. preferably, bacteria. either whole or fragments thereof, including both gram positive and gram negative bacteria, fungi, algae. viruses and other microorganisms are also analytes. as well as animal (e.g., marnmalian) and plant cells and tissues to be analyzed for. e.g., genetic. medical. veterinary, agricultural, forensic, pathology or archeological purposes.

As used herein. the term. "DNA detector molecule(s)" refers to oligonucleotides in the form of hybridization probes. preferably double stranded. that are preferably immobilized to a solid support to form a "panel" of DNA detector molecules. These probes preferably include the polymorphic VNTR regions or other DNA segments representative of individuals or species. These may include, for example, the DNA fragment of Epstein-barr Virus spanning from about nucleotide 7421 to 8042 sequences encoding viral glycosidases. reverse transcriptases, integrases, and proteases, sequences of the long terminal repeats of viral particles, and sequences of specifically representing a particular characteristics of the species/ individuals, to name but a few.

The artisan will also appreciate that the use of the term, "DNA" in describing the VNTR detector molecules or probes according to the invention is not intended to be limiting. Thus, optionally, these probes can be prepared from, or can be used to detect or characterize, any suitable nucleic acid materials able to hybridize to any complementary, hybridizable nucleic acid molecule(s), including, for example, RNA and/or DNA and/or DNA-RNA hybrid molecules, and may further include, for example, non-naturally occurring nucleic acids. For example. the term includes nucleic acids chemically derivitized by art-known methods and art known moieties (e.g., derivatives as disclosed by 37 C.F.R. § 1.822(p)(1), incorporated by reference herein).

As used herein, the term "complementary" with respect to nucleic acid strands is well understood in the art to refer, in part, to nucleic acid strands that are hybridizable to one another so as to form an at least partially double stranded nucleic acid. The more stringent the conditions under which the hybridization process is conducted, the closer the homology required for successful hybridization. The artisan will appreciate that the basis for all complementation is Watson-Crick base pairing in which A pairs with T/U and G pairs with C between two respective nucleic acid strands. A single strand of nucleic acid, e.g., DNA or RNA can be used as a template to prepare its complement. Under ideal conditions, a complementary nucleic acid strand so produced is a complete. i.e., 100 percent accurate, transcript of its template, although nucleic acid strands of less than perfect complementation are able to hybridize and bind under certain conditions.

Hybridization process conditions can be selected which favor high stringency, i.e., conditions under which only nucleic acid strands with a perfect or substantially perfect complementarity will hybridize, or low stringency, which allows, depending on the conditions, hybridization between strands having a range of less than perfect complementation.

While not wishing to be bound by any theory or hypothesis concerning the relationship between the completeness of hybridization, the stringency of the process and the degree of complementarity between a probe and analyte, the following discussion is provided. In order for two nucleic acid strands to hybridize and anneal to each other, the nucleic acid strands must have certain degree of sequence complementarity. Otherwise, under stringent wash conditions, the binding will not be stable and the probe or analyte will be washed away. If two different sequences, e.g., probe and analyte, do bind to each other with certain degree of affinity, relative to control measurements. this typically correlates with a degree of complementary homology between these two sequences.

Under certain unusual conditions anomalous binding between probe and analyte might occur by the formation of hairpins. or loops in one or more strands, e.g., due to the presence of complementary sequences at certain regular intervals along the respective strands. Therefore, a normal Michaelis hyperbolar binding curve might not be observed. Nevertheless, regardless of the type of binding hybridization binding that may occur, if both authentic (control or defined) specimen and the analyte of interest show the same characteristics of binding with the same probes. the data obtained from these binding assays will be useful for species or individual identification. Thus, if two specimens are considered to be identical. they must be identical in binding with a series of probes in (1) mechanism of binding, (2) kinetics of binding, (3) total of percentage of binding with respect to each probe used. and (4) other parameters such as dissociation or association constants of the binding assays. Therefore, the binding pattern observed on the DNA detector molecule, i.e., the probe array, can be characterized for each nucleic acid to be determined as an analyte, prior to running the analytic screening procedure.

Furthermore, if the binding kinetics of the above minisatellites with the first and second DNA fragments conform to a normal hyperbolar binding curve, it is very likely that these two DNA fragments are identical or virtually identical in sequences. Thus, two analytes are considered identical if they have identical DNA fingerprints by electrophoresis and, moreover, if they also show identical number of copies of shared alleles.

If the minisatellite—fragment binding kinetics differ between fragments, this difference can be controlled (e.g., normalized) for by comparing both the binding pattern on the DNA detector molecule array and the binding kinetics to the same parameters for known genomic fragments.

In one aspect of the invention. simply by way of example, a positive signal can be obtained. in the presence of a suitable analyte, by a process of denaturing and then annealing the analyte and immobilized probe array. This can be conducted by art-known enzymatic processes or, more preferably, by thermal cycling between melting and annealing temperatures, using art known apparatus, e.g., such as commercially available thermal cycling machines from Perkin Elmer, marketed for use in conducting the polymerase chain reaction. Other apparatus that can automatically carry out the heating and cooling processes can also be used. The heating and cooling process can also be carried out adding an automated heating and cooling system to a DNA/RNA synthesizer (not available from commercial sources), or to the cuvette holder of a spectrophotometer (available from commercial sources), or simply carrying out the cooling and heating process in an oven and refrigerator, during each stage of the process.

Detection can then carried out, for example, in a spectrophotometer. spectrofluorometer, luminometer, GC and MS apparatus, and any other suitable art known physical and/or chemical means, using either automated and/or manual methods by means of batch and/or continuous processes. The artisan will also appreciate that the methods of the invention include obtaining quantitative data of known specimens as control analytes to determine the quality of an unknown, and the relatedness among the known and unknown to be determined based on the principle of allele sharing. In one aspect of the invention, detection can be accomplished by pattern recognition by comparing patterns of known quantities or characteristics of one or several control analytes with those of the unknown.

Hybridization by thermal cycling is desirably conducted under stringent conditions, such that hybridization and annealing will occur between single strands of the analyte and single strands of the probe that are substantially complementary each to the other. Preferably, the degree of complementarity ranges from about 80 percent to about 95 percent complementarity. More preferably, the degree of complementarity ranges from about 90 percent to about 100 percent complementarity.

Figure 2:
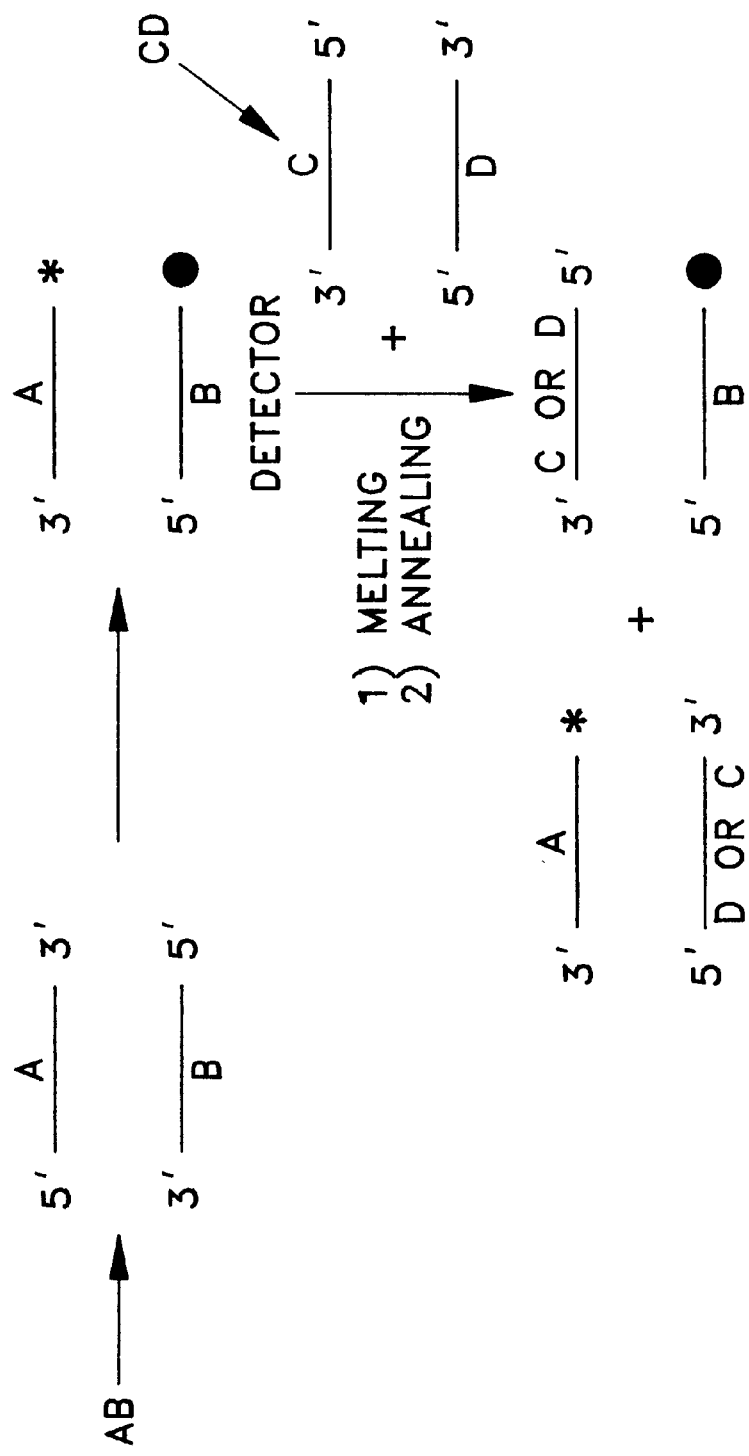
FIG. 2 diagrams a probe dsDNA comprised of strands A and B; wherein B is immobilized to a solid support (solid circle) and A is labeled with a reporter moiety. If CD is homologous to AB. then upon a meltinglannealing cycle. one of C or D will be hybridized to B and D or C will be hybridized to A strands that were displaced from the solid support.

In one aspect of the invention, successful competitive hybridization (the kinetics of which are illustrated in FIG. 2) with the non-immobilized probe strand will result in proportionate signal changes in the assay device, as detectably labeled probe leaves the immobilization surface and moves into the assay medium as displaced single strands or hybridized to the analyte.

In another aspect of the invention, an analyte of interest may be labeled with a reporter moiety and. for example, detected by successful hybridization to immobilized probes on the surface of the device according to the invention.

The artisan will appreciate that the genotyping method according to the invention can be carried out by either forward typing or reversed typing, depending on the availability of the samples or specimens. Using samples obtained from a suspected pathogen. or from samples of a higher organism, e.g., that are collected from the scene of a forensic investigation, either forward or reversed typing may be conducted. When enough specimen is available or polymerase chain reaction ("PCR") amplification products are available for typing analyte nucleic acid material, the typing may be termed as reversed typing. Results obtained from either forward to reversed typing are mutually complementary.

Simply by way of example. the artisan will appreciate that there are at least two ays conduct the identification process according to the invention, based, for example, n the availability of samples such as, e.g., blood. hair, cells, and so forth:

(1) "Forward typing" is the method of using a known DNA sample for genotyping an unknown sample. For example, if a suspect or victim is living and available to investigators, the subject can usually provide as much of the sample (blood, tissue, hair and so forth) as is required for DNA extraction for comparison with an unknown DNA sample (e.g., samples collected from a crime scene).

2) "Reverse typing" is a convenient description in the art for the use of a sample of DNA of unknown origin to screen samples of known origin in order to identify the source of the unknown sample(s). For example, on many occasions, it is likely that the only available samples are unidentified specimens (e.g., blood, hair, cells).

For example, in one aspect of the invention, the process is conducted by heating the detector and analyte above the melting temperature of the DNA/RNA detector probe(s) so that the signal strands of the said device of the claim 1 can be separated from the immobilized strands. Upon cooling below the melting point of the said detector probe(s), the separated signal strands(s) can reanneal back to the immobilized strand(s) in quantitative manner.

In another example, the detector is heated in the presence of restriction fragments of an analyte, having sequences identical to the signal strands or complementary to that of the immobilized strand, by a cycle (or cycles) of heating and cooling, at the melting point of the DNA/RNA detector probe as heretofore described. Upon successful hybridization of the analyte to the immobilized strand, the signal strand of the device is competitively displaced. As a result, the amplitude of the signal on the solid phase of the device is reduced and the amplitude of the signal detectable in the solution phase will be increased.

The artisan will appreciate that by carrying out such competitive binding assays, the percentage of analyte bound ("% B") can be estimated. In addition. the total amount of the analyte that can be bound to the immobilized strand may be determined as follows. The maximum amount of the analyte (% B)max, bound to the detector is calculated from a double reciprocal plot of 1/(% B) verses 1/[analyte], which yields the maximum value of the said device of the claim 1. From the values of the (% B)max, the total number of copy of an allele can be actually determined.

Procedures for attaching reporter moieties, i.e., detectable compounds or labels, to oligonucleotide probes and for preparing such oligonucleotide probes are well known in the art. These procedures are reviewed, for example, by U.S. Pat. No. 5,387,510, supra, citing to Agrawal et al, 1986, Nucleic Acid Res., 14, pp. 6227–45; Levenson et al., 1990, U.S. Pat No. 4,914,210, relating to biotin labels; Levenson et al., 1990, U.S. Pat. No. 4,962,029, relating to enzyme labels, and the references noted therein. All of the foregoing references are incorporated herein by reference in their entireties. Useful reporter moieties also include radioisotopes, electron-dense reagents. chromogens, fluorogens, phosphorescent moieties, ferritin and other magnetic particles (see Owen et al., 1989, U.S. Pat. No. 4,795, 698 and Poynton et al., 1990, U.S. Pat. No. 4,920,061, chemiluminescent moieties and enzymes (which are preferred), electrochemiluminscent moieties, as marketed, for example, by Igen, Inc. (Rockville, Md.) are also contemplated, according to the invention. Useful enzymes include, glucose oxidase, peroxidases, uricase, alkaline phosphatase and any other known in the art. Substrates and reagents for providing a detectable calorimetric, fluorometric or chemiluminescent signal in the presence of a given enzyme label are well known, for example. as described in U.S. Pat. No. 4,994,373, supra.

Conventional methods for the construction of either the immobilized strands or the reporter signal strands are readily employed. Such methods are well known to the art and are described. simply by way of example, by Cros et al., 1996, U.S. Pat. No. 5,510,084: Wu. 1995, U.S. Pat. No. 5,387,510; Stavrianopoulos, supra, the disclosures of which are incorporated by reference herein in their entireties. These methods can be applied, for example, to polymerase chain reaction ("PCR") amplification products or to restriction fragments in order to construct DNA detector molecules.

Preferably, synthetic oligonucleotide probes obtained from an automated DNA/RNA synthesizer are directly employed in the methods of the invention while still attached to the solid support used for synthesis. All further process steps are then carried out on the same solid support without further cleavage of the synthesized VNTR probe. For larger sequences, enzymatic ligation of several smaller pieces of probes are used while still on the solid support. Carrying out all operation steps in a single solid support in one column greatly simplifies all operation steps and eliminates steps such as prehybridization, blottings, linkages, electrophoresis, and other tedious manipulation processes required in the conventional gene probes and the gel banding DNA fingerprinting methods.

Figure 3:
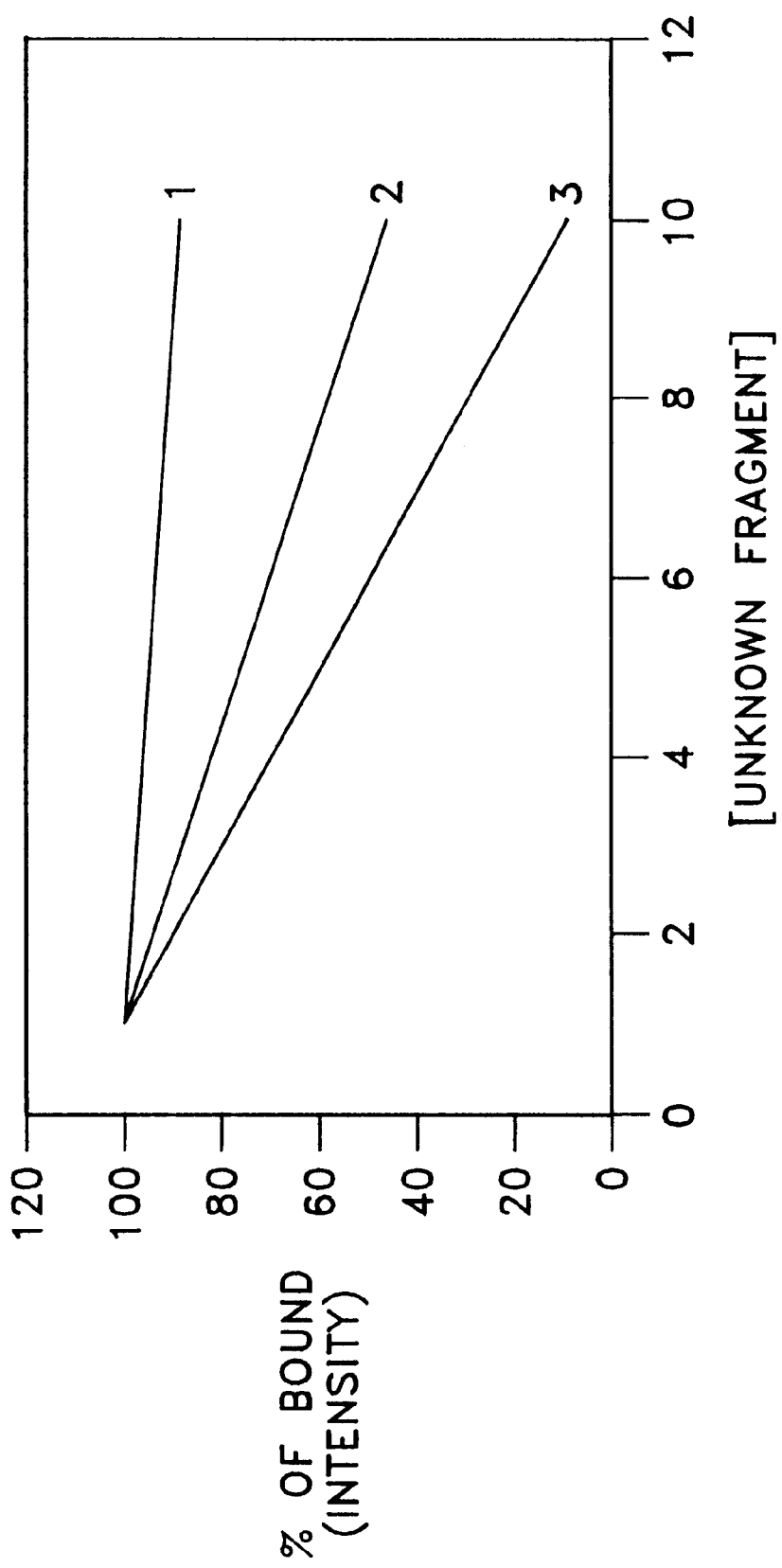
FIG. 3 plots a competitive binding assay where the % of bound oligonucleotide genotyping by the reduction of bound signal strand, plotting the percentage of bound signal strand (by intensity) plotted against the quantity of unknown analyte nucleotide by means of a competitive binding assay.

As can be appreciated from FIG. 3. the DNA detector molecules so constructed consist of multiple copies of the VNTR unit, greatly enhancing the signal to noise ratio and hence, the sensitivity of the detection.

The source of the analyte may be specimens collected from a particular environment and may include animal and/or plant tissue, micro-organisms in free form or present in such tissue samples or cells. The nucleic acid content. e.g., DNA and/or RNA. of a samples is therefore extracted as required, depending on the source of the sample, by art-known methods. Such methods are described, e.g., in U.S. Pat. No. 4,994,373, incorporated by reference, supra.

For instance, for a cellular sample. the targeted cells are extracted and digested with restriction endonucleases using HintI restriction[24] or following the standard method of Maniatis, et al.[25] Any art known restriction endonuclease can be employed according to the invention. and include. simply by way of example, Pst I, HaeIII, AluI, and Taq I. The gene fragments spanning the polymorphic regions are collected and concentrated on a column containing the immobilized strands. Alternatively, the restriction fragments from the target specimen can be used directly without further purification for carrying out the following binding assays.

A mixture containing the immobilized DNA detector molecules and the restriction fragments is then subject to denaturation followed by annealing conditions, e.g., the sample can be heated and cooled above and below, respectively, the hybridization melting points of these nucleic acids.

If the restriction fragments include regions homologous to regions of the signal strands (and complementary to that of the immobilized strand on the solid support), a competition for binding between the labeled and unlabeled and between the bound and unbound for the immobilized strand of the DNA detector molecules will occur, resulting in those restriction fragments that having regions complementary to regions of the immobilized or signal strands being hybridized thereto after a cycle of, e.g., thermal melting and re-hydridization. As a consequence, a proportionate number of the non-immobilized strand of the nucleic acid detector molecule will be displaced into the assay medium. If the non-immobilized strands are linked to reporter moieties, e.g., colorometric or other signaling labels. the degree of homology can then be readily quantified by the amount of the reporter moiety present in the assay medium. Therefore. binding characteristics of the unknown sequences with the nucleic acid detector molecules can be monitored either from the reduced signals in the immobilized or solid phase or by enhanced signals in the assay medium or liquid phase due to the competitive release of the signal strands from the solid phase.

If the specimen contains the same repeats but varies in the total number of the TR's, competition for binding can occur but to a different extent. When the restriction fragments show no shared sequence homology, no competitive binding occurs under stringent wash conditions.

The expression "hybridize under stringent conditions" to describe the hybridization of nucleic acid molecules encompassed within the scope of this invention refers to hybridizing under conditions of low ionic strength and high temperature for washing, for example, 0.15M NaCl/0.015M sodium citrate/0.1% NaDodSO4 at 50° C., or alternatively the presence of denaturing agents such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate, at 42° C. for hybridization.

The expression "hybridize under low stringency" refers, simply by way of example, to hybridizing at 42° C. in 20% formamide, 5×SSC, 50 mM sodium phosphate pH 6.8, 0.1% sodium pyrophosphate, 5×Denhardt's solution, and 50 µg/ml salmon sperm DNA, and washing with 2×SSC, 0. 1% SDS at 42° C.

Variables affecting stringency include, for example, temperature, salt concentration. probe—sample homology and wash conditions. Stringency is increased with a rise in hybridization temperature, all else being equal. Increased stringency provides reduced nonspecific hybridization. i.e., less background noise.

Of course, the artisan will appreciate that the stringency of the hybridization conditions can be varied as desired, in order to include or exclude varying degrees of complementation between probe and analyte, in order to achieve the required scope of detection. For example, under certain conditions, it might be desirable to conduct the method of the invention under less than stringent conditions in order to detect genomic material for which the probe was not initially designed. e.g., a previously known pathogen that has been so mutated at certain alleles by nature or by an opponent that it might not be detected under stringent conditions.

Therefore, the method according to the present invention provides a positive signal for identification of alleles based on hybridization sequence homology rather than a simply a size similarity and electrophoretic properties of the restriction fragments.

In addition. as will be appreciated by the artisan, the binding characteristics of the restriction fragments can also yield significant information concerning structural characteristics of the TR's present in the unknown restriction fragments. Under non-stringent wash conditions the fragments may compete for binding, yielding anomalous curves which can provide additional identifying characteristics.

Reporter moieties for the detection of an analyte comprising a nucleic acid complementary to the detector molecules can be any art known reporter or signalling moiety that can be linked to a nucleic acid strand. Simply by way of example, such a signalling moiety can be a selected to be a fluorochrome, luminescent compound, radioisotope. enzyme, and/or any other art-known chemical or physical indicator suitable for construction of the signal strands of the nucleic acid detector molecules. Simply by way of example, any colorometric signal known to the art, employing any of a rainbow of colors can be employed for signalling hybridization to the nucleic acid detector panel for identification of alleles of unknown specimens of interest. Therefore, detection can be achieved visually and/or by photographic or electronic optical methods.

The compositions and methods according to the invention also have military applications for biological warfare agent detection and treaty verification, as well as significant applications in diagnostic assays, the forensic sciences, and other biological sciences.

DNA SEQUENCES OF SIGNIFICANCE FOR GENOTYPING

Since 1985, Edgewood Research, Development and Engineering Center ("ERDEC") has established a biotechnology program for investigation of the feasibility of application of nucleic acid probes for biological detection. A recent publication by Dr. Yu et al.[29] clearly demonstrated that DNA probes are applicable for biological detection. However, the DNA probes used by Dr. Yu, et al. are conventional multiplex single locus probes, which yield little information as to what has been detected. The present invention provides unexpected advantages in applying the superior VNTR markers (minisatellites, microsatellites, midisatellites) to an array of immobilized, double stranded nucleic acid hybridization probes for genotyping, with detection confirmed, e.g., by displacement of the non-immobilized strand.

Simply by way of example, the devices and methods according to the invention may be usefully applied to detection of pathogenic virus strains under emergency conditions in the field, where regular laboratory facilities are unavailable. One such virus that is useful to illustrate the application of the methods of the invention is the Epstein-Bar virus ("EBV"). EBV is etiologic for mononucleosis, and can transform human lymphocytes into immortalized lymphoblastoid cells. EBV region 7421–8042. The EBV genome also contains 3×type A, repeats, 2×B repeats, 2×D repeats. 3×39 bp repeats from 100665 to 100781 region. The 102581 to 102652 region contains a semi-repetitive sequence similar to human c-fos 3' sequences of the following structure: AAGCCCCACC ATCCGCTGCC GCCCTCCAT (SEQ ID NO:1) and gAGGCCCCACC gTCCGCTGCC GCCCCTCCTT (SEQ ID NO:2), respectively, that are useful for identification of EBV by the methods of the invention.

Adenoviruses also share extensive nucleotide homology. Thus, EBV, adenoviruses and other art known viruses consist of largely unique sequences bracketed by inverted repeats. Strains of the related viruses differ only in the number of the inverted terminal repeats. The simple sequences such as (CA)8, (CT)8, (GTG)5, (GACA)4, (GATA)4. (AAAAA... ), (ACACA) have been shown to be abundantly distributed, and are useful for identification of these viral genomes by DNA fingerprinting.

The DNA sequence of EBV at the repeat region from 7421 to 8042 (having 21×30 bp repeats, as already noted above) is shown in (A) as follows. The unit of the corresponding complementary sequence of A is shown as B. Both A and B can be prepared by an automated DNA synthesizer (note: if necessary, with additional help from DNA ligase or other enzyme systems) or prepared from restriction fragments or PCR products. According to the processes and devices of the invention, the sequence A is immobilized at its 3' end on a solid support, e.g., the controlled pore glass ("CPG") solid phase (through a molecular spacer. if necessary). Sequence B is labeled with a reporter molecule (luminescent molecule, fluorochrome, radioisotope, or a color marker exhibiting any of a rainbow of color) at its 5' end or 3' end and is used as the signal strands in the construction of the DNA detector molecules.

In the example shown. about 21 of the signal strands (reporter labeled sequence B) are required to saturate the immobilized sequence A (total 630 bp long). "A" and "B" are defined as follows.

{atat[a,g][a,g,c]at[t,g]g ggatagcata t[g,a,c]ctaccc[a,g] g}$^{21}$-(s) . . . (A)(SEQ ID NO:12)

{gcgc[g,a][g,a,t]gc[c,a]a aagcgatgcg c[a,g,t]tcgttt[g,a]a} * . . . (B)(SEQ ID NO:13)

Therefore, the actual constructed "DNA detector molecules", i.e., hybridization probes prepared using the polymorphic region of EBV spanning from 7421 to 8042 (630 bp) DNA of EBV (reading 3' to 5') strand, containing 21 tandemly linked repetitive units with reporter moieties on each of the 21 repetitive units having unit sequences as shown in "B" above, labeled with reporter molecule ("*"). In this embodiment, "A" is a genomic DNA strand or fragment immobilized at, e.g., the 5' terminus, to a solid support As can be appreciated by the artisan, unlike the conventional VNTR gene probe detection systems (as described above), that use only one labeled probe at a time, the present detection method using polymorphic repetitive sequences for detector molecule construction contains multiple copies of the detector molecule (from 2 to 100 or greater), which substantially enhances the signal to noise ratio. As a consequence, the signal to noise ratio and detection sensitivity is increased, from about two-fold to about 100 fold, or greater, relative to conventional gene probe detection systems and DNA fingerprinting methods.

For example, with reference to the panel of representative probes illustrated by Table 1. a virus having a genome identical to that of EBV must contain restriction fragments (C/D) identical to A and/or B. Other strains of EBV will have the same TR units. Their major differences. however. are in having variable numbers of the tandem repeats.

As can be seen from FIG. 2 (based on the examples of strands A and B given hereinabove), if AB=CD, by mixing AB and CD together, followed by a cycle (or cycles) of melting and annealing steps, all copies of the signal strand B will be finally replaced by the unlabeled C or D. if a sufficient amount of C or D is present, which will result in the reduction of the overall signal of the immobilized phases from 100% to 0% (Curve 3, FIG. 3). On the other hand, if CD is not identical with AB in sequence, no A can be replaced by either C or D. The original AB signal will remain almost constant (Curve 1, FIG. 3). When CD is not completely identical but shares about 50% of the total number of the repeating unit with AB, the competitive binding curve is shown in Curve 2. The signal of the original AB will be reduced up to final 50%, if sufficient amount of C or D is present in the reaction mixtures.

Similarly in forensic cases, if AB is prepared from a suspect (or original prototype species) and CD is obtained from specimen(s) found at the crime scene (or species to be identified), the present genotyping method will demonstrate that if CD is derived from the suspect. C or D will completely displace B from A. As can be appreciate from FIG. 3 concentrations of C or D increased, the signal generated from AB decreased until approaching the final limit of zero. In the genotyping assays, if CD is not derived from the suspect, C or D can not replace B or A from AB. No reduction of signal from the solid phase can be observed. If C or D can partially replace B from AB, it indicates the specimen obtained from the crime scene is derived from someone related to the suspect but definitely not from the suspect.

CONSTRUCTION OF NUCLEIC ACID DETECTOR MOLECULES

Nucleic acid detector molecules can be constructed and arranged for genotyping by pattern recognition by any suitable art known methods. The oligonucleotides incorporated into the detector according to the invention are nucleic acid strands that are preferably denatured into single-stranded form, and directly fixed to a suitable solid support and the strand bearing the reporter moiety hybridized thereto.

The present invention also encompasses indirect fixation of the analyte, such as in situ techniques where the cell is fixed to the support and sandwich hybridization techniques where the analyte is hybridized to an oligonucleotide sequence that is fixed to the solid support. FIG. 1 illustrates the basic process for immobilizing one strand of a ds DNA molecule at the 3' terminus on a solid support (o), wherein the non-immobilized strand is labeled with a reporter moiety (*) and is displaced from the solid support after a melting/annealing cycle allows analyte nucleic acid to compete with labeled strands for hybridization sites. Release of reporter moiety from the solid support is then detected.

A solid support for the detector molecule(s) may be opaque, translucent, transparent or a combination thereof, in whole or in part. It is preferred that the solid support to which the detector molecules are fixed be nonporous and transparent, such as glass, or alternatively, plastic, polystyrene, polyethylene, dextran, polypropylene and the like. Conventional porous materials, e.g., nitrocellulose filters, although less desirable for practice of the method of the present invention, may also be employed as a support.

For example oligonucleotides can be prepared starting with diethylphosphoramidites synthesized as described by Beaucage et al., 1981, *Tetrahedron Letters* 22:1859–1862, the disclosure of which is incorporated herein by reference in its entirety. One method for synthesizing oligonucleotides on a modified solid support is described in U.S. Pat. No. 4,458,066, incorporated herein by reference in its entirety. One can also use a nucleic acid fragment that has been isolated from a biological source, such as, for example, a restriction endonuclease digest.

Thus, any suitable nucleic acid, from a synthetic or natural source, can be readily attached to a solid support by art known methods for the practice of the present invention. Methods of attaching nucleic acids to a solid support, include, for example, that described by Saiki et al., 1989 *Proc. Natl. Acad. Sci. USA* 86:6230–6234, the disclosure of which is incorporated by reference herein in its entirety, which consists in coupling a 400 base poly(dT) tail to the 3' end of an oligonucleotide or probe and in immobilizing a nucleic acid by means of this poly(dT) tail on a nylon filter by exposure to ultraviolet radiation. so as to effect covalent coupling of the thymine bases to the primary amines present in the nylon. Another art known method of nucleic acid immobilization is described by published international patent application WO 88/01302, the disclosure of which is incorporated by reference herein in its entirety, which describes coupling a ligand, such as an aminoalkyl, to the terminal end of an oligonucleotide and then attaching the free end of this ligand to a solid support, such as polystyrene or the like, by formation of a covalent bond.

In a further aspect of the invention, the support can be a particulate material as described by EPA-0 200 133 (published 1986), which, for example, describes the attachment of oligonucleotides to water-insoluble particles of less than 50 micrometers in diameter, for use in hybridization assays.

Various linking groups for attaching polynucleic acids to glass, polystyrene and latex particles are described in WO 88/01302 (published 1988).

Thus, the attachment of the nucleic acid to a solid support. in single stranded or double stranded form, can be by direct attachment or by indirect attachment via an intermediate. Desirably, the nucleic acids are of sufficient length, e.g., at least about 25 bp, to allow stable hybridization with the complementary nucleic acids of the analyte. The polynucleotide are preferably selected so that the immobilized strand is complementary to the genomic sample or polynucleotide sequence to be detected.

In the process according to the invention, a fragment of nucleic acid, in this case a double stranded ("ds") DNA of interest was rendered single stranded by thermal denaturation. A portion of the single stranded DNA molecules were immobilized at their 3' ends, while the other portion of the mixture was labeled with reporter moieties (reporter moieties can be selected from, e.g., fluorescent, luminescent, isotopes, enzymes, and others well known to the art) at the 5' ends or 3' ends. By mixing the immobilized and labeled free strands together and lowering the temperature below the annealing point, a product of a ds DNA having one strand immobilized and the other strand labeled with a reporter moiety was obtained. The labeled strands of the newly generated "DNA detector" can be repeatedly denatured and reformed by thermal cycling.

The availability of the polymorphic VNTR's has facilitated the construction of these detector panels so that all genotyping procedures can be executed simultaneously on the same panels. Table 1, below, shows a model system of a detector panel that consists of 20 selected DNA detector molecules AA', BB' and PP', where A. B and P are strands immobilized and the corresponding complementary strands A', B' and P' are labeled with reporter moieties.

TABLE 1

A Panel Of Detector Molecules
Arranged In Specific Positions

| I | II | III | IV | |
|---|---|---|---|---|
| AA' | BB' | CC' | DD' | 1 |
| EE' | FF' | GG' | HH' | 2 |
| II' | JJ' | KK' | LL' | 3 |
| MM' | NN' | OO' | PP' | 4 |
| QQ' | RR' | SS' | TT' | 5 |

In Table 1, A through Q denote a series of immobilized DNA sequences and A' through Q' represent the corresponding complementary sequences labeled with reporter molecule. In this "direct" method, the final product is preferably not be cleaved from the solid support in the synthetic column. Instead, the column is preferably used "as is" in the final product form, for subsequent construction of a panel of the "DNA detector molecules." Immobilization processes can be carried out by numerous other methods as already reported in the art.

Thus, Table 1, above, illustrates a model panel of detector molecules according to the invention, i.e., hybridization probes, in the form of a panel that consists of 20 selected DNA detector molecules such as, AA', BB' and PP'. A, B and P are immobilized strands and the corresponding complementary strands A', B' and P' are labeled with reporter moieties. The sequences of these DNA fragments used for constructing a panel of the detector molecules are hypervariable sequences of tandem repeats that are selected to provide a hybridization profile that is unique for each individual or species. The artisan will appreciate that A', B' P' can be labeled with different signal moieties, e.g., distinct colors (or fluorochromes or other chemical and physical indicators) so that genotyping procedures may readily be carried out even in the absence of any sophisticated instrumentation.

For example Fisher and Caruthers[28] have demonstrated that almost any color can be produced by subtle substitution of the central carbon atom of triaryl methyl cations. The color of acidic solutions containing the cations is influenced by the nature of the aryl substituents. And thus, the colors used can be expanded from blue to red and the degree of signal reduction or enhancement can be monitored visually, electronically or by photographic means, for positive identification.

In the presence of unknown DNA fragments having sequence homology with those shown in the panel, competition for binding for the immobilized strands will take place. As a result, the labeled signal strands on the DNA detector will be displaced, resulting in either enhanced signals, in solution phases, or decreased signals in the solid immobilized phases. The increases or decreases of the signals in each position of the panel indicate the degree of sequence among the competitive fragments of the known and unknown. The binding patterns can be correlated as to the identity of individual species and the relatedness among individuals/species.

For example, if a polymorphic VNTR fragment obtained from an individual shows binding pattern such as 1-1 (100%), 1-2 (50%), 11-3 (100%), III-5 (25%), and IV-3 (100%) having the binding percentage shown in the parenthesis, and if the DNA binding pattern of an unknown specimen exhibits exactly the same binding pattern and the same degree of binding characteristics. it can be concluded that the specimen is derived from the same individual or species.

If the pattern of binding and the degree of binding characteristics are only partially matching, it can be concluded that the specimen may be derived from a person related to the individual but not from the individual. Thus, the individual can be excluded as source of the specimen. "Alleles-sharing coefficients" (D) (Note, it is not "bandsharing"). The methods of the invention also allow for the estimation of similarity indices(x) for quantifying the differences between two DNA binding profiles In a further advantage of the present invention. a variety of panels can be readily designed and constructed for special studies related to a particular group of species or individuals. The inventive method for genotyping identification of analytes depends not only on the pattern of binding but also relies heavily on the actual binding characteristics of the genomes of individuals or species with respect to the VNTR sequences employed as probes. Thus, by using hybridization for the assay, the results depend strictly upon on sequence information rather than on size similarity for detection, while avoiding the necessity for actual sequence determinations.

For purposes of the present invention, two species are considered to be identical when:
1) they have the same set of shared alleles: and
2) all binding characteristics of all shared alleles are identical in nature (e.g., binding pattern and binding kinetics) with a standard deviation within allowable limits.

Two species are considered to be not identical:
1) when they do not have any shared alleles as detected by the panel of, e.g.,1; or
2) if they do have shared alleles but none of the shared alleles show any similar binding characteristics.

Two species are considered to be related to each other when
1) they have shared alleles as detected by the panel: and either;
2) they have other. non-shared, alleles:
3) the binding characteristics of the shared alleles are not identical.

As can be appreciated from Curve 1, FIG. 3 is a control curve, which indicates that the sequence of CD is completely different from AB. Therefore, in the presence of CD, the colored labels on AB cannot be replaced by CD, and thus the observed color intensity in AB remains almost unchanged. Curve 2, FIG. 3 shows that CD and AB shares about 50% sequence analogy, in other words total number of VNTR unit is about of that of AB. As consequence, only 50% of the colored labels on the detector AB can be replaced by CD. Curve 3, FIG. 3 indicates that both CD and AB contain identical number of VNTR sequences. As a result, CD can completely replace the colored labels on AB, and when the CD concentration increases continuously, all colored labels on AB can be replaced, in the presence of sufficient amount of CD, as can be seen at the end point of the genotyping process.

Figure 4:
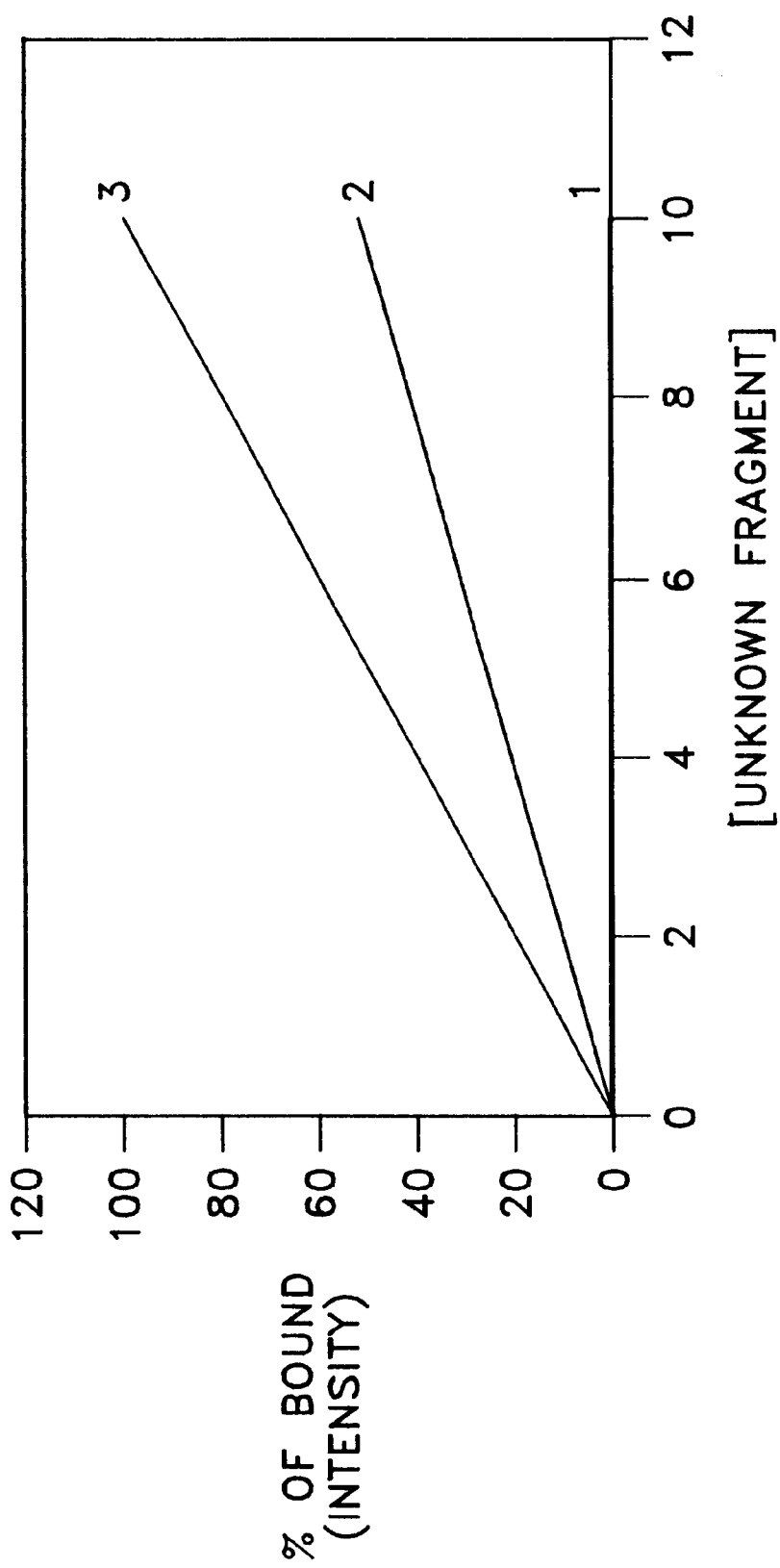
FIG. 4 diagrams genotyping by enhancing bound signal strand, wherein the percentage of signal strand oligonucleotide bound to the solid support (the AA strand of FIG. 3) is plotted (by intensity) against the quantity of unknown analyte nucleotide (illustrated by the CD strand of FIG. 2).

The signal released into the solution from the solid phases can also used for monitoring the binding characteristics between AB and CD. FIG. 4 shows the curves obtained when typing is performed by monitoring the enhanced signal released into the solution from the immobilized solid phase. Curve 1, FIG. 4, shows that CD is completely different in sequence from AB. Curve 3 indicates perfect match between CD and AB. Curve 2 indicates AB and CD share 50% of sequence homology.

The artisan will appreciate that DNA screening data bases can be expanded from gel electrophoretic DNA fingerprints of individuals and species, a data base can be established for each species and individuals as to total number of each VNTR sequence present in the genomic constructs of such individuals and/or species. Such a data base will provide extremely useful information, for analysis of genetic linkage of species and individuals, for study of the effect of the effects of environmental factors on speciation, for investigation of population dynamics and origins of species, for diagnosis of diseases of microbial origin, and many other applications.

EXAMPLES

The following examples serve to provide further appreciation of the invention but are not meant in any way to restrict the effective scope of the invention.

Example 1

Methods for the Preparation of DNA Detector Molecules

A. Construction of Immobilized Strands of the Detector Molecules

I. Preparation of VNTR Hybridization Probes

Oligonucleotides were synthesized on an automated Beckman Oligo 1000M DNA Synthesizer and all reagents were provided by the Beckman. The synthetic procedure as commenced in a column containing a porous silica gel solid support with an initial first nucleoside (CA, dC, dG, dT) attached thereto, by means of a phosphate backbone or a polylinker at the 3' end. Subsequent nucleosides were added one at a time consecutively to the 5' end of the growing oligonucleotide. The sequence addition of each of the nucleosides was controlled automatically through menu-driven software using a keypad and display screen, as described in the Beckman operation manual. A sequence having a length larger than 100 bases may optionally be prepared by linkage of fragments having less than 100 bp using DNA ligase or transferase or the like, while the first synthesized initial strand is still attached to the CPG solid support of the column.

The following sequences of minisatellites have been prepared as described above.

TABLE 2

| Name | Length (Bases) | Sequences |
|---|---|---|
| 33.15 | 32 | 5'-AGAGGTGGGCAGGTGGAGAGGTGGGCAGGTGG-*A (SEQ ID NO: 3) |
| 33.6 | 22 | 5'TGGAGGAGGGCTGGAGGAGGGC-*F (SEQ ID NO: 4) |
| MS1 | 26 | 5'-5'-AGGGTGGA(CT)AGGGTGGA(CT)AGGGTGGA*-K (SEQ ID NO: 5) |
| CMM101 | 30 | 5'-TCCACCTCAGCCCCCTCCACCTCAGCCCCC-*P (SEQ ID NO: 6) |
| YNH24 | 31 | 5'-AACAACCCCACTGTACTTCCCACTGCTCCTG-*L (SEQ ID NO: 7) |
| EFD52 | 27 | 5'-TACTAGCAC(AT)(CG)(CT)CCTGG(CT)TACTAGCAC*q (SEQ ID NO: 8) |
| TBQ7 | 31 | 5'-TGCCTGAGCCTTCTCACAGTCTCACCTGATC-*R (SEQ ID NO: 9) |

TABLE 2-continued

| Name | Length (Bases) | Sequences |
|------|----------------|-----------|
| MS43 | 25 | 5'-CCTTCCCGGGGCCCTCCCTATACCC-*S (SEQ ID NO: 10) |
| JE46 | 17 | 5'-CCCCCCGTGTCGCTGTT-*T (SEQ ID NO: 11) |

These are minisatellites used frequently in the forensic laboratory for individual identification such as, e.g., paternity testing. The starred letters, *A, *F, *K, *P, *L, *R, *S, *T, represent colored and highly fluorescent labels such as, ethidium bromide, propidium iodide, fluorescein thiocyanate, eosin, 4'-6-diamidino-2-phenylindole, indole-3-acetaldehye, hypericin(red), and biotin, respectively. The probes were end-labeled at either the 5'- or 3'- end of the probes using the FluoroAmp Oligonucleotide Labeling systems (Promega) with amino or thiol modified probes. Of course the artisan will appreciate that the labeling may be accomplished by any art-known means. Many other types of satellite DNA are well known to the art and are readily employed according to the present invention. Table 3, below, illustrates representative microsatellite DNA as listed in the National Institutes of Health GenBank.

TABLE 3

Representative microsatellite DNA sequence motifs shown in NIH Gen Bank.

| Sequences of | Frequency reported in the GenBank | | | |
|---|---|---|---|---|
| | *n = 25 | n = 30 | n = 50 | n = 100 |
| a | | 489 | | 3 |
| c | | 8 | | |
| at | | 454 | | |
| ca | 2284 | 1859 | 1164 | 2 |
| cg | 1 | 0 | | |
| ct | | | 292 | 2 |
| ca ct | | 16 | | |
| ct ca | 97 | 72 | 18 | 4 |
| cac | 40 | 14 | | |
| cgg | 36 | 23 | | |
| ctc | 51 | 31 | | |
| ctg | | 61 | | |
| gaa | | 32 | | |
| gaca | | 18 | | |
| gata | 59 | 67 | | |
| ggat | | 10 | | |
| gggca | | 1 | | |
| t taggg | | 17 | | |

*Where n = number of bases. As can be seen, an mono to quadruplet repetitive units are abundantly present.

The artisan will readily understand that any other suitable microsatellite or minisatellite sequence motiffs may be utilized according to the present invention.

II. Immobilization Through Biotin-Streptavidin Reaction Mechanism

Synthesis of biotinylated primers at their 5'-ends using a water soluble biotin ester has been described.[21] The attachment of biotin to DNA fragment also can be accomplished by art known methods using a biotinyl phosphoramidite reagent.[22] Coating a solid support, e.g., microtitre wells, magnetic beads, nylon film. and the like, with streptavidin enables the capture and immobilization of the biotinylated DNA fragments.

Using these fluorescence labeled minisatellites, we have done in situ hybridization with DNA collected from blood. Results indicated that these probes have high affinity for human DNA. The labeled probes in the DNA-probe complexes can be competitively replaced by analogous DNA isolated from individual/species according the competitive binding reaction mechanism as predicted in FIG. 3.

III. Preparation of VNTR Hybridization Probes Using Genomic Fragments or PCR Amplification Products Alternatively, PCR (polymerase chain reaction)[23] products or restriction fragments from the VNTR regions can be used directly for DNA detector molecule construction. The processes include DNA extraction and endonuclease digestion. PCR and any other art known amplification method may be utilized when only a limited quantity of DNA is available, e.g., as in cases of forensic sample analysis. Methods of extraction of DNA or RNA vary with sources and types of cells according to "EDNAP standards". e.g. using Hinfl restrictions[24] or following the standard method of Maniatis, et al.[25] Other restriction endonucleases such as Pst I, HaeIII, Alul, or Taq I etc. have also been widely used. To achieve the goal. PCR products or restriction fragments can be rendered single stranded and immobilized through 3' end to the controlled pore glass (CPG) solid support. The ORG derivatised with a long chain alkylamine with a primary amino loading of about 100 $\mu$ mole/g is available from commercial sources (Pierce Chemical Company). Reacting the long chain alkylamine derivatised CPG with 5'-O-dimethoxytrityl deoxyribonucleoside-3'-succinates in the presence of dicyclohexylcarbodiimide yields the nucleoside CPG column. which is also available from numerous commercial sources (Beckman, for example).

One of the unique features of the present method of detection is that commercially available nucleoside derivatized solid supports, used for synthesis of oligonucleotides are applied directly for construction of the immobilized strands of the DNA detector molecules. The immobilized strands of the DNA detector molecules can be also used for capturing and concentrating VNTR fragments obtained from individuals and species for identification or relatedness determination.

When a polylinker is needed for the purpose of maximizing binding efficiency, a desired length of polylinkers can be added to the solid support using an automated DNA/RNA synthesizer as described supra. Products or fragments prepared by, e.g., PCR, can then be added to the immobilized polylinkers by DNA ligase or DNA transferase or any other suitable art known other enzyme system. Since all of these reactions were carried out in a single column with solid support, reagent additions and washing steps can be performed directly within the column by either a manual or automated process. The "one pot" operation system is straightforward, saving many steps that are required in classical gene probe and DNA fingerprinting methods.

IV. Methods of Immobilization to Other Supports

Immobilization to polylipids. polymeric microspheres, magnetic beads, microtitre wells, nylon film, and other solid supports have been very well documented in the art. For example, U.S. Pat. No. 5,387,510, supra, incorporated by reference herein in its entirety, provides a review of many of the art-known methods of attaching nucleic acid molecules to a solid support, as does U.S. Pat. No. 4,994,373 supra, also incorporated by reference herein in its entirety.

B. Linking DNA Detector Molecules to Reporter or Signal Moieties

I. Biotinyl and Phosphotvrosinyl Phosphoramidite Linkage.

Biotinyl and phosphotyrosinyl phosphoramidite derivatives are useful in the incorporation of multiple reporter groups on synthetic oligonucleotides. Simply by way of example, a 5'-amino group can be added to a probe with the Aminolink II reagent (Applied Biosystems). For the Examples provided hereinbelow, a biotin residue was attached to the amino group using a water soluble sulfo-NHS-biotin ester (Pierce Chemical Co.) and the biotinylated oligonucleotide was purified by reversed phase HPLC.[22]

II. DNA fingerprinting with radioactive and digoxigenated oligonucleotide probes complementary to simple repetitive DNA sequences has also been described, e.g., by Weising et al., 1991[26], incorporated herein by reference in its entirety. The artisan will readily appreciate that the methods described by Weising et al. are readily applied to the practice of the invention.

III. A general method for efficient non-isotopic labeling of DNA probes cloned in M13 vectors with biotin-11-dUTP has also been described by Macedo et al.[27] The artisan will readily appreciate that the methods described by Macedo et al. are readily applied to the practice of the invention.

IV. Recently, a series of DNA/RNA minor groove intercalating agents have been found to have significant antiviral activity. The anti-viral activity of nucleic acid minor groove intercalating agents have been under intensive investigation by Prof. Tsai of Kent State University, using molecular similarity analysis and structure-activity relationship studies. Dr. Tsai and his co-workers have reported that interaction of certain anti-viral agents with nucleic acids can enhance the antiviral and anticancer drug action. These intercalating agents have been used in clinical laboratories for construction of assay systems having sensitivities reported to have reached a detection limit of 600 molecules. Therefore, the artisan will appreciate that the invention further provides for the use of such DNA/RNA intercalating agents, in combination with MLP's prepared according to the invention, to provide simultaneous inactivation and detection of biological agents. In a further variation, such intercalating agents are also optionally employed as DNA reporter molecules for genetic typing by the processes and devices as disclosed here.

Example 2

Purification of DNA from Whole Blood of an Unnamed Individual

Sample Preparation

The isolation of a nucleic acid analyte from a human blood samples is exemplified as follows. In brief blood cells donated by an individual were lysed and the DNA fraction was collected, separated from RNA and proteins, and amplified by PCR. Further details are provided below.

1. Materials

Cell Lysis Solution was prepared with 0.2 M NaOH and 1% SDS. Cell resuspension solution was prepared to contain 50 mM Tris-HCl, 10 mM EDTA, and 100 µg/mi RNAase A. Column wash solution for Wizard plus mini-preps system contains 190 mM potassium EDTA. Direct purification buffer includes, 50 mM KCl, 10 mM Tris-HCl, pH 8.8, 1.5 mM MgCl, 0.1% Triton X-100, guanidine-HCl, 7 M (100 ml) and guanidine-HCl 4.5 M/isopropanol, 40%. The neutralization solution contains 1.32 M potassium acetate. pH 4.8. TE buffer contained 10 mM Tris-HCl, pH 7.5 and I mM EDTA.

2. Methods of Sample Collection and Preparation a. Whole blood was collected in tubes containing EDTA.

b. 300 µl of Cell Lysis Solution was added to a sterile 1.5 ml microcentrifuge tube containing 300 µl of whole blood and mixed well, with inversion. for about 5–6 minutes.

c. The mixture was then incubated for 10 minutes at room temperature, during which time the tube was inverted 2–3 times to lyse the cells.

The sample was then centrifuged at 13,000–16000 g, for 20 seconds, at room temperature and thereafter the supernatant was removed and discarded. The lysis procedure was repeated, when necessary.

d. 300 µl of Nuclei Lysis Solution was added to the precipitate at the bottom of the centrifuge tube and the resulting suspension was pipeted 5–6 times to further lyse the white blood cells. The mixture was incubated at 37° C. until cellular clumps were disrupted. The procedure was then repeated with an additional 100 µl of Nuclei Lysis Solution for another hour.

e. 1.5 µl of RNase Solution was added, followed by incubation for 15 minutes to remove RNA.

f. 100 µl of protein Precipitation Solution was then added and the mixture was vigorously vortexed for 10–20 seconds, followed by centrifugation at 13,000–16,000 g to remove proteins.

g. The clear supernatant was thereafter transferred to a clean 1.5 microcentrifuge tube containing 300 µl of isopropanol. The mixture was gently mixed, followed by centrifugation to precipitate DNA threads.

h. The supernatant was decanted and 300 µl of 70% Ethanol was added at room temperature., followed by gentle washing of the precipitate and further centrifugation (13,000–16,000 g) to precipitate the DNA.

The ethanol was carefully removed by aspiration, so as to avoid disturbing the pellet,. The DNA pellet was then air dried for about 10–15 minutes.

i. 100 µl of DNA Rehydration Solution (10 mM tris-HCl/l mM EDTA, pH 7.4) was then added to the tube and the tube was incubated at 65° C. for 1 hour.

j. The resulting DNA preparation was stored at about 2–8° C.

Example 3

Hybridization of Genomic DNA with Probes in Solution

1. Reagents

Hybridization buffer for use with synthetic probes was freshly prepared from the following components:

3 ml 10% PVP (polyvinylpyrrolidone);

3 ml 10% BSA;

3 ml 10% Ficoll 400;

15 ml 20×SSC buffer stock; and the above mixed with water to a final volume of 150 ml.

SSC Buffer 20 X:NaCl was prepared from:

NaCl, 3 M 175.3 g Na-citrate-2.H20, 0.3 M, 88.2 g

The pH was adjusted to 7.0 with 1 M HCl

Water was then added to a final volume of I liter

2. Hybridization in Solution

In the presence of 500 µl of hybridization buffer, 1–2 µg of genomic DNA and 1–2 µg of one of the probes set forth in Table 2, above. To this solution was added 50 µl of 10 M NaOH. 300 μl of 2 M Tris. pH 7.4, and 475 μl of 1 M HCl (added dropwise, with swirling to provide gentle mixing). The mixtures were then incubated at 85° C. overnight.

The next day, the mixture was cooled to room temperature and the genomic DNA-labeled DNA-probe complexes were purified through a Wizard minipreps DNA Purification Resin (Fisher Scientific, Inc.) according to Promega Technical Bulletin No. 117, the disclosures of which are incorporated by reference in their entirety.

Estimate of Total Bound Copies of Probe Per Copy Of The Genomic DNA:

Data were obtained by titration of 1 μg of the genomic DNA with the labeled fluorescent probes with an added concentration of 100 ng. The above-described purified DNA-labeled probe complexes were analyzed for total probe bound (to genomic DNA) with respect to total amount of probe added, and the percentage of probe bound (% B) versus total amount of probe added was plotted to obtain the values of total amount of probe and thus total copy of probe bound per copy of the genomic DNA to be estimated. For example, a plot of total amount of a labeled DNA probe (33.15) bound versus concentration in ng of probe added produced the following data (percent bound is "% B" and weight added probe in ng is "WtP".

TABLE 4

| Probe 33.15 | | Probe 33.6 | | Probe YNH24 | |
|---|---|---|---|---|---|
| % B | WtP (ng) | % B | WtP (ng) | % B | WtP (ng) |
| 0.56 | 20 | 0.62 | 20 | 0.40 | 20 |
| 0.77 | 40 | 0.88 | 40 | 0.52 | 40 |
| 0.92 | 60 | 1.04 | 60 | 0.56 | 60 |
| 0.98 | 80 | 1.15 | 80 | 0.68 | 80 |
| 1.03 | 100 | 1.23 | 100 | 0.61 | 100 |

For example, if a double reciprocal plot is prepared from the data of Table 4, for probe 33.15 (figure not shown), the maximum amount of DNA of minisatellite probe 33.15, that can be bound to a copy of the genomic DNA, is estimated from the intercept at the Y-axis. Based on the above date, the reciprocal plot of 1/% B (Y axis) verses 1/ng (X axis) produces a straight line intersecting the Y axis at about 0.75, yielding the value of the maximum percent of 33.15 bound to the genomic DNA ["(% B)max"]. Based on the instant data. the (% B)max was found to be about 1.3% of the 100 ng of added 33.15 DNA, that is, about 1.3 ng of 33.15 DNA was bound to 1 μg of the genomic DNA. Assuming the average of size of the genomic DNA is about 50 kd long, a total of 21 copies of 33.15 DNA (about 32 bp), was be bound to the genomic DNA. Similarly, the maximum values of % B of 33.6 and YNH24 that can be bound to the genomic DNA were found to be 1.6 and 0.7 ng, respectively. Thus, the total number of copies of 33.6 DNA and YNH24 DNA that can be bound to a copy of the genomic DNA was about 37 and 12, respectively. The binding assays were carried out using microscope slides as solid support and the values of % B were estimated from measurements taken with an epifluorospectrophotometer (Internation Diagnostic Technology).

TABLE 5

| Name of Probe | (% B)max | Copy of Allele/Copy of Genomic DNA |
|---|---|---|
| 33.15 | 1.34 | 21 |
| 33.6 | 1.6 | 37 |
| YNH24 | 0.7 | 12 |

These results, including the data of Table 5, clearly indicate that the total allelic profile of a genomic DNA can be estimated without the use of the tedious and time-consuming gel electrophoretic and other laboratory procedures as necessary in the conventional multiplexing and DNA fingerprinting methods. The information obtained from these binding assays is quantitative with respect to each individual/species, which can provide useful data to support information obtained from conventional DNA probe methods. As will be appreciated by the artisan. this significant information simply cannot be obtained from electrophoretic DNA gel banding profiles. heretofore employed.

METHODS FOR PCR AMPLIFICATION OF ANALYTE

Nucleic acid analyte samples and other nucleic acid materials were amplified by the polymerase chain reaction as follows.

Five microliters of cell lysate (ca. 2×104 DNA molecules), 25–50 ng of purified DNA, or 1/20 of stain extract was about sufficient to conduct a PCR reaction. The PCR mixtures contained: 10 pmol of biotinylated primer 50 pmole of unbiotinylated primer. the four dNTPs at 0.2 mM concentration and 1.25 units of *Thermus aquaticus* (Taq) DNA polymerase (Promega Biotech) in 50 μl of 50 mM tris-HCl buffer (pH 8.8), 15 and 0.01% gelatin (Taq DNA polymerase buffer). The PCR reaction was initiated with a "hot" start by first heating the sample for 5 min at 95° C., followed by addition of the Taq DNA polymerase at 80° C. Thirty PCR cycles of 1 min at 95° C., 1 min at 58° C. (markers, ADH3. ARSB, Meth, and LDLR) or at 54° C., and 1 min at 72° C. were carried out in test tubes or microtiter plates wells in a programmable heat block (MJ Research). "Multiplex" PCR with two or more primer pairs in one reaction was carried out under the same conditions, with 10 pmole of each biotinylated prime, and 50 pmol of each unbiotinylated primer, and 2.5 unites of Taq DNA polymerase.

Application of Method

Using DNA isolated from hair from the same individual (Kawasakiu, E S, Sample preparation for blood, cells, and other fluids, in Innis, M A, Gelfand, D A, Sninsky, J J, White. J J, eds, PCR Protocols. a guide to methods and applications, Academic Press Inc., pp. 146–152.), we were able to further identify that the DNA isolated from hair of the same individual showed the same binding characteristics as indicated above. Unlabeled hair DNA can completely replace the bound probes attached to genomic DNA isolated from blood, as predicated by FIG. 3.

Numerous references are cited throughout the present patent specification, the contents, both within the text and as footnotes referring to the following list of reference, all of which are incorporated herein in their respective entireties.

REFERENCES

1. Jeffrey, A J. Wilson V. Thein S L. Hypervariabale 'minisatellite' regions in the human DNA, Nature 314.67–73, (1985).
2. Bretten R J. Kohne D E, Repeated sequences in DNA, Science 161. 529-MO (1968).
3. Singer E N. Jeffreys A J, Both "hot" and "cold" transcripts of minisatellites 33.15 and 33.6 produce informative DNA fingerprints in pigs, Fingerprint News 2, 3–7 (1992).
4. Dixon AF, Anzeenberger G, Monteiro DA, Cruz MAO, Tateli I, Jeffreys AJ (1992), DNA fingerprinting of free-ranging groups of common marmosets (*Calliithrix acchus jacchus*) in N E Brazil. In Paternity in primates: Genetic tests and theories. Martin, R D, Dixon, A F, Wickings, E J (eds) Basal, Karger, 192–202.
5. Vassart G, Georges m, Monsieur E H, Hypervariablie minisatellites in human and animal DNA. Science 235, 683–684 (1987).
6. Vergenaud G., Gauguier D, Schott J J, lepetit. D., Lauthier V, Mariat D and Buard J, (1993) Detection, Cloning, and distribution of Minisatellites in some mammalian genomes. In DNA Fingerprinting: State of Science, Pena J D et al (ed), Berhauseor Veriag Basel/Switzerland, 47–57.
7. No reference 7.
8. Gilber D A, lehman n, O'Brien Sj, wayne R K, Genetic fingerprinting reflects population differentiation in the California Channel Island fox. Nature 344,764–766, 1990.
9. Macado A M, Mealo M N. gomes R F, Pena S D J, DNA fingerprints; a tool for identification and determination of the relationships between species and strains of Leishman is. Mol Bioch Par 53: 63–70, (1992).
10. Signer and Jeffreys, application of human minisatellite probes to the development of informative DNA fingerprints and isolation of locus-specific markers in animals. in DNA Fingerprinting; State of the Science. eds Jeffreys et al., 1993, Birhauser Verla Basel/Switzeland. 421428.
11. Wong et al., 1987, Characterization of a panel of highly variable minisatellites cloned from human DNA. Annu. Hum. genet. 51:269–288.
12. Gilbert V. Michel G. Monsieur R. Brocas H, lequarre A S. Christophe D. A sequence in M13 phage detects hypervariable minisatellites in human and animal DNA, Science 235. 683–684 (1987).
13. Stalling R L, Ford A F, Nelson D, Tomey D C, Hidebrand C E, Moyzis Rk. Evolution and distribution of (GT)n repetitive sequences as a general source for polymorphic DNA markers. Nucleic Acids Res 17; 6463–6471(1989).
14. Meyer W, koch A, Neimanen C. Beyermanen B, Eppalen J T, Bomer T. Differentiation of species and strains among filamentous fungi by DNA fingerprinting. Curr Genet 19, 239–242 (1991).
15. Meyer W, koch A, Neimann C. Beyermann B, Epplen J T, Bomer T. Differentiation of species and strains among filamentous fungi by DNA fingerprinting. Current Genet 19, 239–242 (1991).
16. Jeffreys, A J, Brookfield J F Y Semenoff R. Positive identification of an immigration test- case using human DNA fingerprints., Nature 317, 818–819 (1985).
17. Nybom H, Schaal B A, DNA 'fingerprints' applied to paternity analysis in apples (Malus x domestica). Theor Appl Genet 79: 763–768, 1990.
18. Nybom H. Hall H K, Minisatellite DNA fingerprints can distinguish Rubus cultivars and estimate their degree of relatedness. Euphytica 53:107–114, 1991.
19. Chakraborty R and Jin L. a unified approach to study hypervariabale polymorphisms: Statistical Consideration, in DNA Fingerprinting: State of the Science, Ed. Jeffrey. et at., 1993, Bihkhauseres Vereslag, Basel Switzerland).
20. ERDEC Scientific Conference. 1995.
21. Bengtstrom, M, Jungell-Nortamo A. Syvanen A-C (1990) biotynylation of oligonucleotides using a water soluble biotin ester. Nucleosides Nucleotides 9:123–127.
22. Misiuresa K. Durrant I, Evans M R, gait Mj (1990) Biotinyl and phosphotyrosinyl phosphoramidite derivatives useful in the incorporation of multiple reporter groups on synthetic oligonucleotides. Nucleic Acids Res 18: 4345–4354.
23. Saiki R K. Scharf S. Faloona F. Mullis K S, Horn G T, Erlich H A, Arnheim N (1985) Enzymatic amplification of beta-globin sequences and restriction analysis for diagnosis of sickle cell anemia. Science 230; 1350–1354.
24. Schneider P M, Fimmeress R, Woodroffe S., Werrett D J, Bares W., Srinkrnann B. Eriksen B. Jones S., Kloostermann A D, Mevag B., Pascali V I, Ritineres C., Schmitter H., Thomson J A, Gill R. (1991) Report of a European collaborative exercise comparing DNA typing results using a single locus DNA probe. Forensic Sci tnt 49:1–15)
25. Maniatis T. Fritsch E S. Sambrook J (1982) Molecular cloning: A Laboratory Manual. Cold Spring Harbor Laboratory, Cold Spring Harbor, N.Y.), p73.
26. Weising K. Beyermann B, RamserJ, KahI G (1991) Electrophoresis 12:159–169.
27. Macedo A M, Medeiros A C, Rena S D J (1989): application to DNA fingerprinting. Nucleic Acids Res 16:10394.
28. Fisher. E. F. and Caruthers, M. H. (1983) Nucleic Acids Res. 11, 8031. (Also see, Oligonucleotide Synthesis, a practical approach (1984) M J gait, Ed., IRL Press, Oxford, Washington. D.C. pp.75.)
29. Yu H, Smeno J G, Cheng T-c. Calomiris J J, Goode M T, and Gatto-Menking D L (1995) J Biolumin Chemilumin 10, 239–45.

What is claimed is:

1. A device for detecting or characterizing a nucleic acid analyte, said device comprising a panel of double stranded oligonucleotide probes immobilized on a solid support, each probe having a first strand comprising a hypervariable number of tandem repeat sequences and a second strand complementary to said first strand, said probe being selected to hybridize to at least one allele of said nucleic acid analyte and comprising a fragment of an Epstein-Barr virus genome spanning from about nucleotide 7421 to about nucleotide 8042.

* * * * *